(12) United States Patent
Hanina et al.

(10) Patent No.: US 11,961,620 B2
(45) Date of Patent: *Apr. 16, 2024

(54) METHOD AND APPARATUS FOR DETERMINING HEALTH STATUS

(71) Applicant: AIC Innovations Group, Inc., New York, NY (US)

(72) Inventors: Adam Hanina, New York, NY (US); Daniel Glasner, New York, NY (US)

(73) Assignee: AIC Innovations Group, Inc., New York, NY (US)

( * ) Notice: Subject to any disclaimer, the term of this patent is extended or adjusted under 35 U.S.C. 154(b) by 760 days.

This patent is subject to a terminal disclaimer.

(21) Appl. No.: 17/089,544

(22) Filed: Nov. 4, 2020

(65) Prior Publication Data

US 2021/0057105 A1    Feb. 25, 2021

Related U.S. Application Data

(63) Continuation of application No. 15/682,366, filed on Aug. 21, 2017, now Pat. No. 10,861,605.
(Continued)

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/0077* (2013.01); *A61B 5/0205* (2013.01);
(Continued)

(58) Field of Classification Search
CPC ...... G16H 50/20; G16H 50/30; A61B 5/0022; A61B 5/0077; A61B 5/0205; A61B 5/1118; A61B 5/165; A61B 5/7267
See application file for complete search history.

(56) References Cited

U.S. PATENT DOCUMENTS

| 4,852,988 A | 8/1989 | Velez et al. |
| 6,652,458 B2 | 11/2003 | Blazey et al. |

(Continued)

FOREIGN PATENT DOCUMENTS

| WO | WO 2001/074236 | 10/2001 |
| WO | WO 2016/022414 | 2/2016 |

OTHER PUBLICATIONS

EP Extended Search Report for App No. EP 17844239.8 dated Jul. 25, 2019 (10 pages).
(Continued)

*Primary Examiner* — Christopher A Flory
(74) *Attorney, Agent, or Firm* — Fish & Richardson P.C.

(57) ABSTRACT

A system and method for monitoring the state of an individual. The method includes providing a stimulus to the individual, measuring a response to the provided stimulus, comparing the measured response to an expected response, and diagnosing one or more aspects of disease in accordance with the result of the comparison between the measured response and the expected response. The stimulus may be a predetermined test sequence, such as a visually displayed predetermined sequence of images, or may include observation of the physical response of the individual while performing one or more predetermined activities. Stored images or video of the individual responding to one or more test sequences may be stored in a lossy or lossless state, and thus security and de-identification may be provided to stored data. This stored data may also be de-identified in a manner to allow for the answering of the greatest number of future questions.

16 Claims, 17 Drawing Sheets

Related U.S. Application Data

(60) Provisional application No. 62/531,703, filed on Jul. 12, 2017, provisional application No. 62/505,627, filed on May 12, 2017, provisional application No. 62/419,763, filed on Nov. 9, 2016, provisional application No. 62/377,818, filed on Aug. 22, 2016.

(51) Int. Cl.

| | | |
|---|---|---|
| *A61B 5/0205* | (2006.01) | |
| *A61B 5/11* | (2006.01) | |
| *A61B 5/16* | (2006.01) | |
| *G16H 10/60* | (2018.01) | |
| *G16H 20/00* | (2018.01) | |
| *G16H 50/20* | (2018.01) | |

(52) U.S. Cl.
CPC .......... *A61B 5/1118* (2013.01); *A61B 5/4833* (2013.01); *A61B 5/68* (2013.01); *A61B 5/7267* (2013.01); *G16H 10/60* (2018.01); *G16H 20/00* (2018.01); *G16H 50/20* (2018.01); *A61B 5/0022* (2013.01); *A61B 5/0035* (2013.01); *A61B 5/162* (2013.01); *A61B 5/163* (2017.08); *A61B 5/165* (2013.01); *A61B 2562/0219* (2013.01)

(56) References Cited

U.S. PATENT DOCUMENTS

| | | |
|---|---|---|
| 7,359,214 B2 | 4/2008 | Heard |
| 8,408,706 B2 | 4/2013 | Yahav |
| 8,538,775 B2 | 9/2013 | Skomra |
| 8,666,781 B2 | 3/2014 | Hanina et al. |
| 8,731,856 B2 | 5/2014 | Kitamura et al. |
| 8,731,961 B2 | 5/2014 | Hanina et al. |
| 8,831,299 B2 | 9/2014 | Kurtz et al. |
| 9,183,601 B2 | 11/2015 | Hanina et al. |
| 9,256,776 B2 | 2/2016 | Hanina et al. |
| 9,454,645 B2 | 9/2016 | Hanina et al. |
| 9,652,665 B2 | 5/2017 | Hanina et al. |
| 10,861,605 B2 | 12/2020 | Hanina et al. |
| 2009/0012419 A1 | 1/2009 | McKee |
| 2009/0048871 A1 | 2/2009 | Skomra |
| 2012/0219176 A1 | 8/2012 | Guan |
| 2012/0316897 A1 | 12/2012 | Hanina et al. |
| 2013/0128990 A1 | 5/2013 | Narasimhan |
| 2013/0169781 A1 | 7/2013 | Hanina et al. |
| 2013/0321772 A1 | 12/2013 | White et al. |
| 2014/0086462 A1 | 3/2014 | Shan |
| 2014/0343450 A1 | 11/2014 | Stack |
| 2014/0364761 A1 | 12/2014 | Benson et al. |
| 2014/0371544 A1 | 12/2014 | Wu et al. |
| 2014/0371599 A1 | 12/2014 | Wu et al. |
| 2015/0135325 A1 | 5/2015 | Stevens et al. |
| 2015/0178469 A1 | 6/2015 | Park et al. |
| 2015/0238120 A1 | 8/2015 | Shan |
| 2017/0049319 A1 | 2/2017 | Simmons |
| 2017/0367633 A1 | 12/2017 | Samadani |
| 2018/0052971 A1 | 2/2018 | Hanina et al. |

OTHER PUBLICATIONS

Goodfellow, Ian, et al. "Generative Adversarial Nets" Advances in Neural Information Processing Systems 27 (NIPS 2014) pp. 1-9.

Newton. Preserving Privacy by De-Identifying Facial Images. Mar. 2003. [Retrieved on 07 Oct. 1-18, 2017]. Retrieved from the Internet: <URL: http://reports-archive.adm.cs.cmu.edu/anon/2003/CMU-CS-03-119.ps> pp. 1-26.

PCT International Search Report and Written Opinion for Intl App No. PCT/US2017/047896, dated Nov. 3, 2017 (13 pages).

Shrivastava, Ashish, et al. "Learning from Simulated and Unsupervised Images through Adversarial Training." arXiv preprint arXiv:1612.07828 (2016) (16 pages).

METHOD AND APPARATUS FOR DETERMINING HEALTH STATUS

CROSS REFERENCE TO RELATED APPLICATIONS

This application is a continuation of U.S. patent application Ser. No. 15/682,366, filed Aug. 21, 2017, which claims the benefit of the following U.S. Provisional Patent Applications, the entire contents thereof being incorporated herein by reference:

U.S. Provisional Patent Application Ser. No. 62/377,818, filed Aug. 22, 2016, to Hanina, titled "Method and Apparatus for Determining Health Status";

U.S. Provisional Patent Application Ser. No. 62/419,763, filed Nov. 9, 2016, to Hanina et al., titled "Method and Apparatus for Storing Information";

U.S. Provisional Patent Application Ser. No. 62/505,627, filed May 12, 2017, to Hanina at al., titled "Method and Apparatus for Storing and Processing Information"; and U.S. Provisional Patent Application Ser. No. 62/531,703, filed Jul. 12, 2017, to Hanina et al., titled "Method and Apparatus for Visual Diagnostics."

This application also incorporates by reference the entire contents of the material presented in U.S. patent application Ser. No. 13/189,518, filed Jul. 24, 2011, to Hanina et al., titled "Method and Apparatus for Monitoring Medication Adherence" and published as U.S. Patent App. Pub. No. 2012/0316897.

FIELD

The subject matter of the present disclosure relates generally to monitoring patient health status and to the diagnosis and monitoring of disease employing visual images and image analysis, and more particularly to visually monitoring health status by visually or otherwise recognizing one or more characteristics of the patient, and to the use of particular visual analysis tools and models in both active and passive monitoring techniques to diagnose and monitor disease and symptoms of disease as related to particular disease states and patient populations.

The subject matter of the present disclosure additionally relates generally to storing personally identifiable visual information, and more particularly to storing such video information in a manner that allows for analysis of activity, clinical parameters, diagnosis or monitoring of disease, or other desired features, in addition to any desired future analysis of such data, while maintaining the security and privacy of the data. The subject matter of the present disclosure also relates to the use of such stored secured information in the diagnosis and treatment of disease, as well as more generally determining status of an individual based upon the stored data, as noted above.

BACKGROUND

Monitoring patient health status, as well as the diagnosis and monitoring of disease, whether, e.g., during a clinical drug trial, during disease management by a physician, or in home care scenarios, may entail confirming that a patient has administered required medication.

SUMMARY

In U.S. Pat. Nos. 8,731,856, 8,731,961, 8,666,781, 9,454, 645, and 9,183,601, the contents of these five patents being incorporated herein by reference in their entirety, the inventors of the subject matter of the present disclosure have proposed a system, method and apparatus that allow for complete control and verification of adherence to a prescribed medication protocol or machine or apparatus use in a clinical trial setting, whether in a healthcare provider's care, or when self-administered in a homecare situation by a patient.

In U.S. Pat. No. 9,256,776 (the '776 patent), the content of this patent also being incorporated herein by reference in its entirety, the inventors of the subject matter of the present disclosure describe a system for de-identification of one or more images of an individual. The techniques for determination of one or more portions of an image to be de-identified may be applied to the subject matter of the present disclosure, thus reducing required computing load. As will be described below, application of the feature extraction/ keypoint method and system may be applied not necessarily to complete images, but additionally to one or more portions of images as identified in accordance with the '776 patent.

These patents and other patents attributable to the inventors of the subject matter of the present disclosure present the only medication management system that may determine whether a user is actually following a protocol, provide additional assistance to a user, starting with instructions preferably including one or more interactive and real-time audio, visual, textual or the like prompts based upon one or more actions detected of the user, and moving up to contact from a medication administrator if it is determined that the user would need such assistance in any medical adherence situation, including clinical trial settings, home care settings, healthcare administration locations, such as nursing homes, clinics, hospitals and the like, and in clinical trial settings. They also present the only system designed to contextually de-identify images of the face of an individual allowing for review of these images while maintaining the security of these images.

The subject matter disclosed herein builds on these initial inventions and provides one or more features that may be employed in accordance with these systems to use further visual information collected by a video camera or other sensor to determine additional characteristics associated with medication administration or otherwise the health of the patient administering the medication, or any other individual.

The subject matter disclosed herein builds on these initial systems, devices and techniques, and additionally provides one or more mechanisms for collecting and storing visual data related to the users of the system, and in a particular embodiment, video of the users administering medication. In this context, such video may provide a view of the face of a particular user, thus allowing their identity to be determined from these video images. Such determinations may be made on the local device of a user, or at a remote processing location, such as a cloud computing location, or dedicated remote server location. While this information may be stored in a secure manner, through encryption and the like, the inventors of the subject matter disclosed herein have determined that it would be beneficial to implement a system that balanced the need to secure the video data while allowing for future analysis of the data in one or more manners currently not contemplated.

Therefore, in accordance with one or more embodiments of the present disclosure, a system and method are provided in which a video sequence is preferably analyzed to determine a number of features that may be representative of one or more images in a video sequence, such as keypoints or landmarks of the face of a user indicative of the identity, a current health or other state of the user, or other visual features in one or more additional images. Once such features are determined, a subsequent determination may be preferably made to determine a subset of these features that may be maintained which allow for analysis of the video sequence, while being "lossy" enough to de-identify the images by precluding reverse processing of the features to allow identification of the user. Images for use in accordance with the invention may be captured using a camera capture device, such as that in a dedicated camera, a mobile device such as a smartphone, or the like. Analysis processing may employ any methods, such as computer vision analysis, neural networks, deep (reinforcement) learning, machine learning, or the like. Processing may be provided by a processor embedded within such a camera, mobile device, or dedicated computing system. Data transmission preferably takes place over a cellular, Wi-Fi enabled or other wireless or wired communication system.

Additionally, information retrieved from one or more users of the system, whether provided in identifiable or de-identified format, may be used in order to make determinations of diagnosis or monitoring of disease, or other detailed status of an individual, such as determination of pulse rate or other bodily states. Thus, any images obtained of such users may be relied upon in order to determine one or more statuses of a user, whether the images are identifiable, or de-identified. The ability to perform such analysis from a de-identified image ensures proper data protection while allowing for extensive post-hoc analysis of these de-identified images. These images to be analyzed may further be analyzed in other than collected chronological order, this allowing for the analysis of individual frames, or frames having similar characteristics, together regardless of when these images were acquired.

The subject matter of the present disclosure further provides one or more mechanisms for collecting and storing visual data related to the users of a system, and in a particular embodiment, video of users or patients performing one or more predetermined activities (active monitoring), or performing their daily routine activities (passive monitoring). Active monitoring may comprise presentation of a particular visual sequence on a display, and monitoring of a user's response to this visual sequence, such as by tracking or otherwise analyzing the eyes, gaze direction or other facial characteristic of the user. Passive monitoring may comprise observing the user when performing a sequence as instructed by a device, but for the purpose of another activity, rather than the visual sequence displayed as noted above, or by monitoring daily routines that are known to the system in order to measure a response. In this context, such video may provide a view of the face of a particular user, thus allowing for one or more desired characteristics to be viewed and tracked over time. Such characteristic review may be made on the local device of a user, or at a remote processing location, such as a cloud computing location, or dedicated remote server location. This information is preferably stored in a secure manner, through encryption and the like.

Therefore, in accordance with one or more embodiments of the present disclosure, a system and method are provided in which a video sequence of a user performing one or more predetermined activity sequences, or performing routine activities, is analyzed to determine a number of features that may be representative of one or more diagnostic attributes, such as eye movement, affect, heartrate, skin tone and the like. Once such features are recognized and tracked, a subsequent determination may preferably be made to determine a subset or combination of these features that are indicative of diagnosis or monitoring of disease, and may be analyzed over time to determine changes in a particular disease progression.

The subject matter of the present disclosure provides one or more features that may be employed in accordance with these systems to use further visual information collected by a video camera or other sensor to determine additional characteristics associated with the health of a patient, or any other individual.

Images for use in accordance with the subject matter of the present disclosure may be captured using a camera capture device, such as that in a dedicated camera, a mobile device such as a smartphone, or the like. Analysis processing may employ any methods, such as computer vision analysis, neural networks, deep learning, machine learning, or the like. Processing may be provided by a processor embedded within such a camera, mobile device, or dedicated computing system, either local or remote, such as in a cloud-based system. Data transmission preferably takes place over a cellular, Wi-Fi enabled or other wireless or wired communication system.

Additionally, information retrieved from one or more users of the system may be used in order to make determinations of diagnosis of disease, or other detailed status of an individual, such as determination of pulse rate, eye movement, or other bodily states. Thus, any images obtained of such users may be relied upon in order to determine one or more statuses of a user.

Implementations of the subject matter of the present disclosure may have advantages relative to existing systems and techniques. For example, U.S. Pat. No. 7,359,214 includes a device that provides instruction to a patient regarding medications to take. This system, however, provides no mechanism for actually confirming that a patient is in fact properly administering required medication, including, e.g., placing a medication pill into their mouth, or injecting or inhaling medication following a predetermined series of steps, as required in a clinical drug trial, as prescribed by a prescribing physician in the case where adherence to a particular regimen may prove to be critical to efficacy of the prescription regimen, in various public health scenarios, in situations where failure to keep up a prescription regimen can potentially harm a population as a whole, such as the generation of antibiotic-resistant bacteria strains, in various disease management scenarios, or in home care situations where maintaining proper control of administering healthcare professionals is critical. U.S. patent application Ser. No. 11/839,723 (now U.S. Pat. No. 8,538,775), filed Aug. 16, 2007, titled Mobile Wireless Medication Management System provides a medication management system employing mobile devices and an imaging technology so that a user is able to show a pill to be taken to the system, and the system can then identify the medication. Similarly, however, there is in fact no particular manner in which to ensure actual adherence, including ingestion, inhalation, injection of the medication, or the relationship of adherence to the efficacy or safety of the drug over time.

The inventors of the subject matter disclosed herein have determined that diagnosis and monitoring of disease traditionally requires subjective determination of disease state by a healthcare professional. Application of known disease parameters to a currently observed set of disease states from a patient results in a diagnosis of disease. Continued monitoring of these disease states allows for monitoring of disease, and determinations of progression thereof, over time. Medical diagnosis and monitoring systems typically rely on such subjective determinations, or upon measurements made in a controlled environment, such as blood draws in a clinic, x-rays and the like.

The inventors of the subject matter disclosed herein have further determined, however, that prior art systems fail to describe the use of advanced visual analysis to properly diagnose and monitor disease, collecting information from across populations, and determining critical characteristics indicative of such diagnoses. These systems similarly fail to take into account accurate determinations of medication adherence in order to further diagnose and monitor disease.

U.S. Pat. No. 8,408,706 entitled "3D Gaze Tracker" describes a system for determining a gaze of a person, comprising a 3D camera that acquires a range image of a person, a picture camera that acquires a picture of the person, and a controller that processes images acquired by the cameras to determine a gaze direction and origin for the gaze vector of an eye of the person. This complex system is one that is difficult or impossible to implement on a simple mobile device, and requires complex processing of an image being viewed by the person in order to determine the input stimulus being provided to the person.

US Patent Application Serial No. 2013/0321772 entitled "Medical Diagnostic Gaze Tracker" describes a system for detecting a gaze behavior of a user in response to a stimulus, where the stimulus is a non-diagnostic stimulus, determining a type of the stimulus, and generating an indication of the gaze behavior and the type of the stimulus. Thus, while the system is not an active system (i.e., does not provide a predetermined stimulus to the subject) it does require a complex system for imaging the field of view being viewed by a person, and determining a type of input stimulus being observed by the person.

International Patent Application Serial No. WO/2001/074236 describes a system for diagnosing Attention Deficit Hyperactivity Disorder (ADHD). The application in turn relies upon a complex eye tracker system described in U.S. Pat. No. 4,852,988, and comprises a complex system including a helmet to be worn by the person being tested. While this application describes a number of characteristics to be reviewed in diagnosing ADHD, the system suffers from complexity, and the inability to monitor eye movement when viewing a passive, non-predetermined set of visual images, as the system is primarily designed to track the eyes of the person while performing a physical task.

Additionally, existing systems fail to further incorporate the monitoring of any further patient characteristics to aid in determining proper medication adherence, and to further determine a status of the patient.

The inventors of the subject matter of the present disclosure have further determined that these and other existing systems fail to consider that sensitive or other individually identifiable information may be captured and stored by these systems. These existing systems fail to consider confidentiality of any acquired information, and the ability to store this information in a secure, confidential manner while still allowing for future analysis of any such acquired and stored data.

The inventors of the subject matter of the present disclosure have further determined that prior art systems fail to describe the use of such stored data for the purpose of diagnosing or monitoring disease or current status of an individual.

Still other objects and advantages of the invention will in part be obvious and will in part be apparent from the specification and drawings.

The subject matter of the present disclosure accordingly comprises several steps and the relation of one or more of such steps with respect to each of the others, and the apparatus embodying features of construction, combinations of elements and arrangement of parts that are configured to affect such steps, all as exemplified in the following detailed disclosure, and the scope of the invention will be indicated in the claims.

BRIEF DESCRIPTION OF THE DRAWINGS

Reference is made to the following description and accompanying drawings, in which.

DETAILED DESCRIPTION

In accordance with an embodiment of the subject matter of the present disclosure, a visual motion capture device, camera or the like is used to capture motion information related to the administration of pill or film based oral medications, or injectable, inhaler-based, other non-pill based medication, or any other form of patient administration task that may be performed, may be utilized in accordance with one or more of the methods, devices, and systems noted in the above-referenced applications.

Information Capture System

Figure 15:
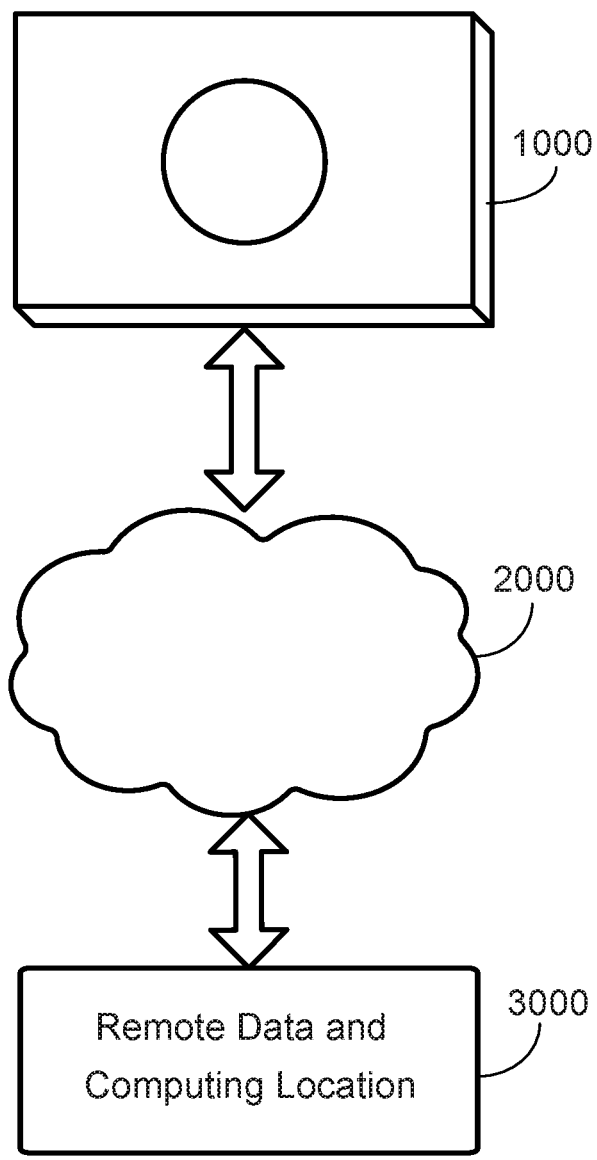
FIG. 15 is a block diagram depicting the details of an exemplary hardware configuration for implementing the subject matter of the present disclosure.

Referring first to FIG. 15, a remote information capture apparatus 1000 is shown. Such apparatus is configured to allow for the capture and processing of information in order to implement the system and method in accordance with the subject matter of the present disclosure. Such information capture apparatus 1000 is preferably placed in communication with a remote data and computing location 3000 via a communication system 2000, preferably the Internet or other communication system. Via communication system 2000, information captured by apparatus 1000 may be transmitted to remote data and computing location 3000, and analysis information or other instructions may be provided from remote data and computing location 3000 to apparatus 1000. It is further contemplated that a plurality of such information capture apparatuses 1000 may be coordinated to monitor a larger space than a space that can be covered by a single such apparatus. Thus, the apparatuses can be made aware of the presence of the other apparatuses, and may operate by transmitting all information to one of the apparatuses 1000, or these apparatuses may each independently communicate with remote data and computing location, which is configured to piece together the various information received from the plurality of devices 1000.

Figure 16:
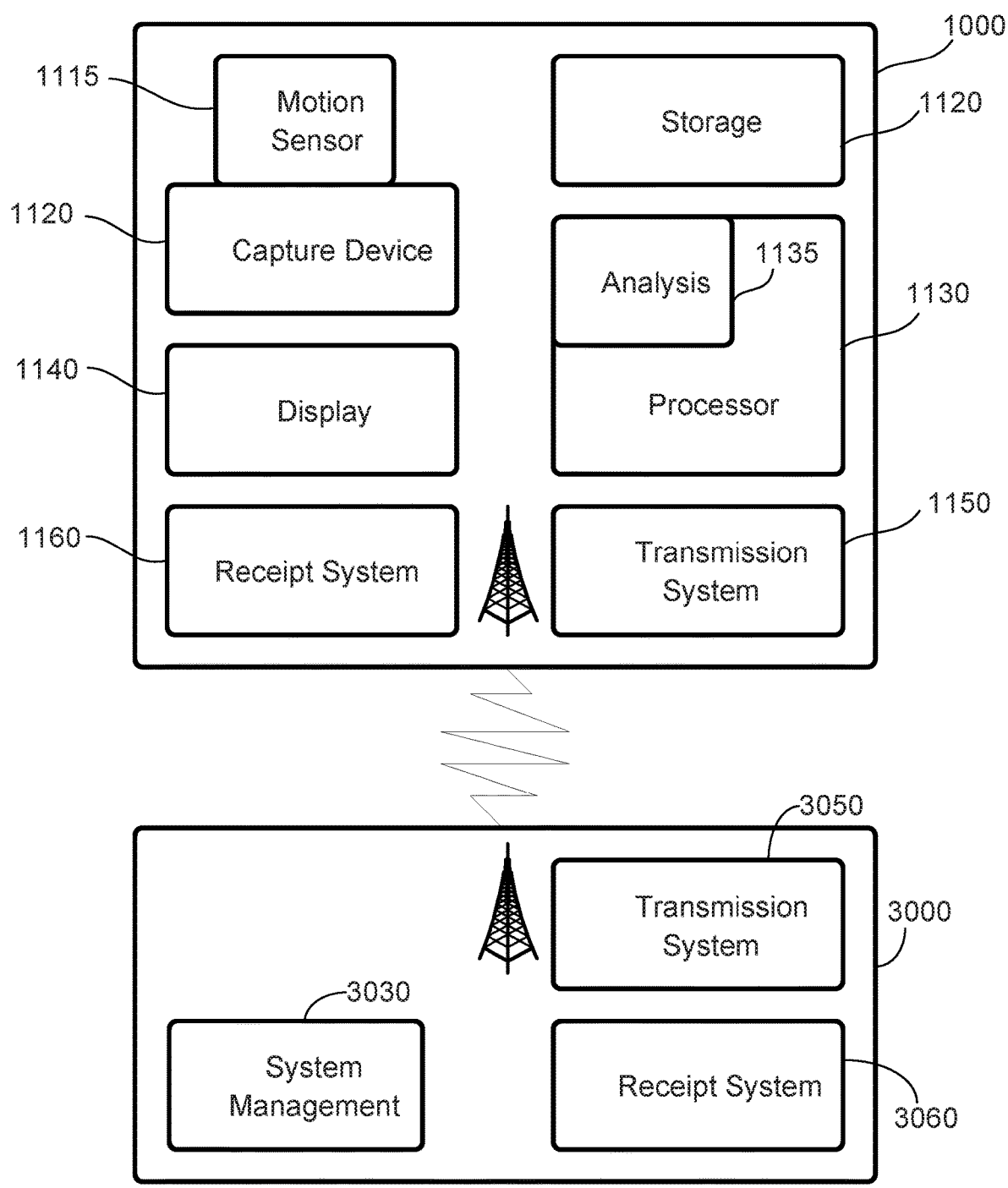
FIG. 16 is a block diagram depicting additional details of an exemplary hardware configuration for implementing the subject matter of the present disclosure.

Referring next to FIG. 16, a more detailed view of a preferred embodiment of remote information capture apparatus 1000 and remote data and computing location 3000. As is shown in FIG. 16, apparatus 1000 comprises an information capture device 1110 for capturing video and audio data as desired. A motion detector 1115 or other appropriate trigger device may be provided associated with capture device 1110 to allow for the initiation and completion of data capture. Information capture device 1110 may comprise a visual data capture device, such as a visual camera, or may be provided with an infrared, night vision, or other appropriate information capture device. A storage location 1120 is further provided for storing captured information, and a processor 1130 is provided and configured to control such capture and storage, as well as other functions associated with the operation of remote information capture apparatus 1000. An analysis module 1135 is provided in accordance with processor 1130 and configured to perform a portion of analysis of any captured information at the remote information capture apparatus 1000. Apparatus 1000 is further provided with a display 1140, and a data transmission and receipt system 1150 and 1160 for displaying information, and for communicating with remote data and computing location 3000. Remote data and computing location 3000 comprises system management functions 3030, and a transmission and reception system 3050 and 3060 for communicating with apparatus 1000. Transmission and reception system 3050 and 3060 may further comprise various GPS modules so that a location of the device can be determined at any time, and may further allow for a message to be sent to one or more individual apparatuses, broadcast to all apparatuses in a particular trial, or being used for administration of a particular prescription regimen, of broadcast to all available apparatuses.

In accordance with an embodiment of the present disclosure, apparatus 1000 is preferably configured to be part of a system that improves adherence to a medical protocol, and to analysis of collected visual data of user medication adherence to determine health status of users. Users of apparatus 1000 in accordance with this system give administrators a tangible and concrete manner in which to review activities and collected information. Apparatus 1000 of the invention is configured to receive instructions for patients from remote data and computing location 3000 and provide these instructions to patients. Such instructions may comprise written, audio or audio instructions for guiding a user to perform one or more activities, such as performing a sequence of actions to test a particular action of the user, or whether a user is adhering to a prescribed medication protocol.

The system, in accordance with an embodiment of the present disclosure, is also applicable to monitoring of patient activities when being requested to perform particular actions, or when performing routine actions not specifically requested. Therefore, in accordance with an embodiment of the present disclosure, a method and apparatus may be provided for analyzing captured patient motion data, preferably in near real time to provide feedback to the user, to determine a number of times a participant performs some action that is, for example, considered suspicious, or to determine one or more elements of diagnosing or monitoring disease.

In accordance with a further embodiment of the present disclosure, the visual capture device 1110 may be used to capture visual information related to one or more subjects. Any standard camera or image capture device may be employed, including but not limited to a camera on a mobile phone, tablet, other computing device, standalone camera, or any other image acquisition apparatus that is able to record one or more (video) images of a subject. In a preferred embodiment of the present disclosure, the subject may comprise a face of a human, but may comprise any other desirable subject, including one or more other body parts of the user, or other object. Analysis of these recorded images may be performed currently, or the images may be stored for future analysis. Storage of such images may be performed local to the image capture apparatus, at a remote location, such as a dedicated storage location, or a cloud based storage system. Storage of these images, however, may present a security problem, and the identity of the subjects or other confidential information in the captured visual information may be discernable from these images. De-identification of this stored information will be described below.

Additionally, visual representations of a user can be further used to determine a status of the user. Visual determination of one or more parameters, such as motion, eye motion, skin tone, emotions, heart rate, blood pressure, body mass, gps location, proximity, or other measurements (such as non-visual measurements) that may be provided in accordance with one or more incorporated or coupled sensor, may be measured visually or otherwise, at once or over time, to determine changes in one more of such parameters in order to identify changes in the health of the user. In accordance with an embodiment of the present disclosure, by way of example, display 1140 preferably displays one or more bits of information to a user. Such information may preferably comprise a specific video sequence designed to test the reaction of the user, or may comprise interactive or other instructions to the user to perform a predetermined activity. Information capture apparatus preferably captures information monitoring the user upon viewing of the displayed information, and performing one or more activities in response thereto. Other devices for capturing information in response to presented visual or other stimuli may include diverse sensors, such a glucose meters, blood pressure cuffs, radar systems, visual capture devices, thermometers, accelerometers (measuring the shake of the hand of a user, for example), or the like. One or more of such measure parameters may be used to identify particular characteristics of one or more disease states. In such a manner, while monitoring adherence or other activities, or when performing actions in response to a presented test script, such parameters may be measured, and reported back to one or more healthcare professionals, one or more care providers, other individuals, or may be collected in order to analyze automatically, perhaps over time, to diagnose and monitor disease. Thus, these parameters may be measured over time without reference to adherence, allowing for diagnosis of disease, measurement of progression of disease once diagnosed, or measurement of various health indicators to gauge the overall health of an individual.

Furthermore, a database or other repository of such measurements may be collected over time and over users at remote data and computing location 3000. Such database may be characterized by disease state or other demographic characteristics. In this manner future measurements of one or more users may be compared against such a database, and allow for diagnosis of one or more diseases, or changes in these characteristics when monitoring these diseases. Furthermore, expected progression of such parameters over time may be determined for a population as a whole, or for various portions of a population, defined by demographics, disease state or the like. So, by way of example, it may be possible to determine expected progression of one or more visual characteristics, such as weight gain, of a female aged 40-60 suffering from diabetes, or to determine expected changes in response to a visual presentation of a script to be followed by a user. Of course, other sub-populations may also be determined from such a database.

In an additional embodiment of the present disclosure, the measured characteristics may comprise one or more de-identified video assets that may be determined from capture of images of a user from connected, integrated or other visual capture apparatus 1110, such as a still or video camera. De-identification of one or more of such captured images allows for further analysis of these images, generating a more robust database, while protecting the identity of any individual originally pictured in the images. Thus, through the generation of derivative images, portions of images, characteristics or the like, information may be stored in a manner that allows for future analysis while protecting the identity of the users. One or more mechanisms for generating such de-identified images will be described below.

In yet a further embodiment of the present disclosure, the determination of whether a particular user has modified disease characteristics may be determined in accordance with one or more unsupervised learning systems, such as a neural network or the like. In such a manner, the database of collected images may be employed to train such a system, identifying one or more characteristics from the training images that may be used to identify similar characteristics in future images. Furthermore, the use of such unsupervised learning techniques preferably provides an additional layer of de-identification of images, allowing for the further collection of images of users, and the subsequent maintenance of these images in a de-identified state through the generation of derivative images, image portions, extracted characteristics and the like that may be stored for comparison to future images processed in a similar manner. Furthermore, data may be further encoded in these images, such as one or more codes associated with a camera device, or other identifying information. Additional information collected from one or more external sensors, such as accelerometers, void recorders, associated with the camera device, or one or more external medical devices, such as glucose meters, heartrate meters, or other measurement devices, or any of the sensors noted in FIG. 4 (as will be described below) may be further included in the unsupervised learning system to additionally encode or categorize images. This collected information may be used to calibrate the system during a learning phase, and may be subsequently removed during an operation phase. Combination of one or more of these readings with visual information may further allow for the determination of additional changes in status of a patient or user.

By way of example, pulse oxymiters, heartrate monitors and the like may be employed with collected video information to allow for more precise determinations. Additionally, micro movements associated with movement of a mobile device or the like may be also be employed. Micro eye movements, gaze tracking, analysis of expression, or any other micro gestures, micro movements, or other recognizable conditions and the like may further be employed. These additional measured features may be further employed to identify changes in characteristics along a number of alternative dimensions in such an unsupervised or supervised learning system, ultimately diagnosing or monitoring disease. Analysis of the accumulated information may allow for identification of one or more common characteristics among or between various disease states, demographic states, or other common identifying characteristic.

Longitudinal analysis of such data and changes in visual and other characteristics over time may be further correlated to negative health outcomes such as hospitalization events or death, and may give rise to relationships that can then act as the basis to trigger interventions in advance of a negative health outcome occurring. Through such monitoring, early warning signs may be extracted from visual images of users in a manner not previously possible. Thus, any number of visual analysis techniques may be employed to generate a video asset base by therapeutic area over time, thus allowing for the user of such assets to evaluate the health of users in the future including similar characteristics, and residing in similar therapeutic areas.

In accordance with one or more embodiments of the present disclosure, it is anticipated that the use of one or more sections of the electromagnetic spectrum will allow for an in-depth analysis of facial or other visible user features. For example, as will be described below, rather than simply noting external facial features, the techniques and systems disclosed herein allow for the determination of the location of various blood vessels under the skin of a user in the field of view of a camera. Over time, differences determined in the various images provide information about the performance of the user, and may further indicate changes in disease, physical ability, or the like. Such changes, for example, may be more visible under near-infrared light, or other wavelength of energy, thus resulting in additional information being extracted based upon the use of multiple types of light, energy, or other data extraction mechanisms.

As will similarly be described below, by overlaying multiple layers of information, irrespective of the amount of information provided in each of those layers, a more concrete picture of the status of an individual may be provided. Information collected from lower power devices may include lower resolution information, such as images with fewer pixels, or may include different mechanisms for data collection. As more information is acquired, either through different collection mechanisms, or as the power of collection improves over time, correlations between collected data and negative outcomes (or positive outcomes) in one or more medical therapeutic areas may be provided. The system may therefore be employed as a diagnostic tool for predicting disease or other diagnosis based upon processing of visual images of a user. By allowing for the use of such varied layers, the system is robust to methods of collection, timing of collection, and storage formats of the information, thus "future proofing" the system to rely on older data (perhaps at lower resolutions), and newer collected data, having a higher resolution, or a newer or new data collection technique.

The inventive system may therefore learn various correlations between one or more observed features, and health status, health outcomes, disease progression, symptom progression, or one or more changes in overall health. By analyzing and correlating these changes in features and ultimate health status, the system provides a mechanism for determining yet unknown relationships between measurable quantities and the health of an individual. Once established, these relationships can then be used to predict future medical situations. By way of example, one or more sub-segments of the population may be targeted for observation. If such population is a post-stroke population, it is known that rapid weight gain may be a symptom of failure to take proper medication, or may predict a more urgent medical situation. In accordance with an embodiment of the present disclosure, daily images of an individual may allow for a determination of such rapid weight gain without the use of a body-weight scale. In such a situation, a healthcare provider may be immediately notified to follow up with the individual. While visual-spectrum features may be used to determine weight gain, determinations of changes in pulse, blood pressure or other measurements may rely on the above-mentioned other areas of the electromagnetic spectrum, audio pulses, or any other type of desirable sensor, whether alone or in concert with a visual analysis.

In accordance with alternative embodiments of the present disclosure, accumulated images of one or more users, associated sensor data information, visually extracted information, and one or more additional inputs may be incorporated into a comprehensive database. Analysis of the accumulated information may allow for identification of one or more common characteristics among or between various disease states, demographic states, or other common identifying characteristic. Thus, in accordance with one or more embodiments of the present disclosure, collected information may be stored in a standard or de-identified format, and used to determine not only current conditions and actions, but also to diagnose disease, changes in health conditions, or to segregate individuals from populations to identify one or more potential medical or other unique conditions. The techniques and systems disclosed herein provide the ability to perform these diagnoses from de-identified information, thus allowing for the protection of personal information while retaining sufficient information to allow for subsequent diagnosis.

As noted above, this accumulated information may be employed to train one or more learning systems, thus further extracting common characteristics or elements to be extracted. These extracted characteristics comprise one or more derivative elements of the accumulated images and other data, and allow for the storage of these derivative elements in a de-identified manner, without the need to store and maintain the images including identifying information. In such a manner, large databases of patient information may be processed, and characteristics extracted therefrom may be used to identify further common characteristics from later acquired images related to medication adherence, or other disease state characterization. The system will therefore be adaptable to diagnose disease, or other changes in patient status simply by taking images of a new user, either in a single shot, or noting changes in any measured characteristics over time.

Longitudinal analysis of such data and changes in visual and other characteristics over time may be further correlated to negative health outcomes such as hospitalization events or death, and may give rise to relationships that can then act as the basis to trigger interventions in advance of a negative health outcome occurring. Through such monitoring, early warning signs may be extracted from visual images of users in a manner not previously possible. Thus, any number of visual analysis techniques may be employed to generate a de-identified video asset base by therapeutic area over time, thus allowing for the user of such assets to evaluate the health or users in the future including similar characteristics, and residing in similar therapeutic areas.

The system may process information at remote system 3000 housing a database of collected information. New images acquired by an image acquisition camera 1110 in local mobile device 1000 may be transmitted to the remote location 3000, one or more of the above-noted identification or processing techniques may be applied, and then the results of such analysis may be provided as feedback to a user or other healthcare provider to provide advanced notice for possible adverse events, changes in health, and predicted outcomes, such as future hospitalizations, worsening of illnesses, particular symptoms or the like. Alternatively, processing may be performed in advance of image acquisition, and then a system for identifying characteristics of a future image may be provided to the local device to further process acquired images. Such a system may be reduced in processing requirements to allow for appropriate processing on the local mobile device. By providing either of these systems in accordance with a medication monitoring process, when monitoring medication administration, other health issues of the user may be diagnosed. Such diagnosis may identify changes in characteristics of a particular disease state, or may identify new diseases or one or more characteristics of any of such diseases.

De-Identification of Information

Figure 1:
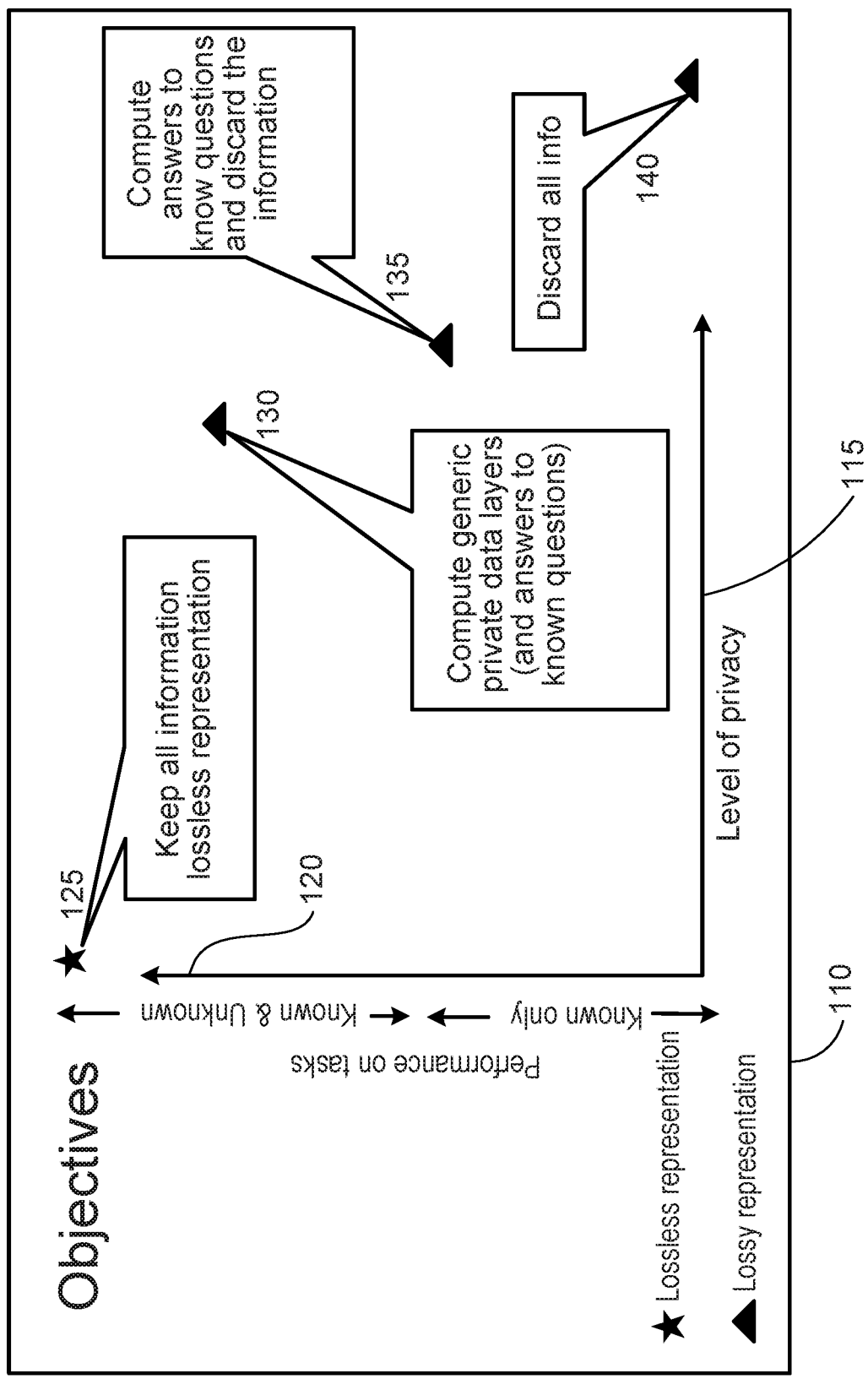
FIG. 1 is a graph depicting information and a tradeoff between levels of privacy and the ability to perform tasks on the information in accordance with an exemplary embodiment of the invention.

Referring next to FIG. 1, a graph depicting a relationship between a level of privacy maintained vs. the ability to perform various desirable tasks is shown. In accordance with an embodiment of the present disclosure, captured information may include one or more images of the face of a user but may comprise an image of any other object. As is shown in FIG. 1, graph 110*a* first horizontal axis 115 corresponds to a level of privacy provided by a particular solution. As one moves further from the origin along horizontal axis 115, an increased level of privacy is provided. A second vertical axis 120 depicts an achievable level of performance on various tasks. Movement further from the origin along vertical axis 120 represents an increase in the level of performance attainable. The vertical axis is further partitioned in two. The bottom (closed) segment corresponds to performance on a fixed set of "known" tasks. The top (half open) segment corresponds to performance on other tasks which we might be interested in down the line but which are not in the "known" set yet.

As is further shown in FIG. 1, four different scenarios for data storage are provided, with a corresponding performance available depicted. A first option is to maintain all collected information in a lossless representation. This option is noted by star 125, and is positioned on graph 110 high on vertical axis 120, representing a high flexibility in processing of data (as all information is available), but scores low on horizontal axis 115 as there is no security provided by processing of this information. This option allows one to attain the best achievable performance on any task known or unknown since none of the information is discarded. For the same reason it provides no inherent privacy.

A second option denoted by lossy triangle 130 allows for the computation of some generic level data layers that have identifying information removed, and also to use the collected original data to answer some known questions before removal of the identifying information. As can be seen in FIG. 1, this option 130 provides relatively high performance on future tasks, and also performs better on the security front. Provided one make a good choice of layers (features/descriptors) this solution allows one to compute answers to the known tasks (possibly limiting the selection of algorithms). If a comprehensive set of sufficiently generic features are selected to be computed, it can also be expected that this configuration is also able to perform well on a wide variety of unknown tasks, those which rely on information which is present in the generic layers. In terms of privacy the layers can be designed to mask private information. The more layers collected and the more generic they are, the more flexibility in answering future queries, but also the greater the possibility that some identifiable information may be gleaned from the stored information.

A third option 135 goes a bit further and simply computes answers to known questions and then discards all of the initially-acquired information. While this provides a further improvement along the security axis, the ability to answer any future questions that might arise is minimal, as there is no further representation of the initially-acquired data to be processed. Computing answers to all known tasks provides more privacy since the data stored is restricted to a minimal set of information. On the other hand, it is unlikely that all queries will be determined up front, and therefore the ability to address many unknown future tasks is low.

Finally, option 140 simply discards all known data after any current processing. While this situation provides the highest level of security, there is no ability to use the information in the future.

The inventors of the present disclosure have determined that option 130 provides the best tradeoff between future processing and security. The subject matter of the present disclosure therefore presents a number of solutions in order to achieve this option along with a system allowing for selectability of the security/future processing tradeoff.

Figure 2:
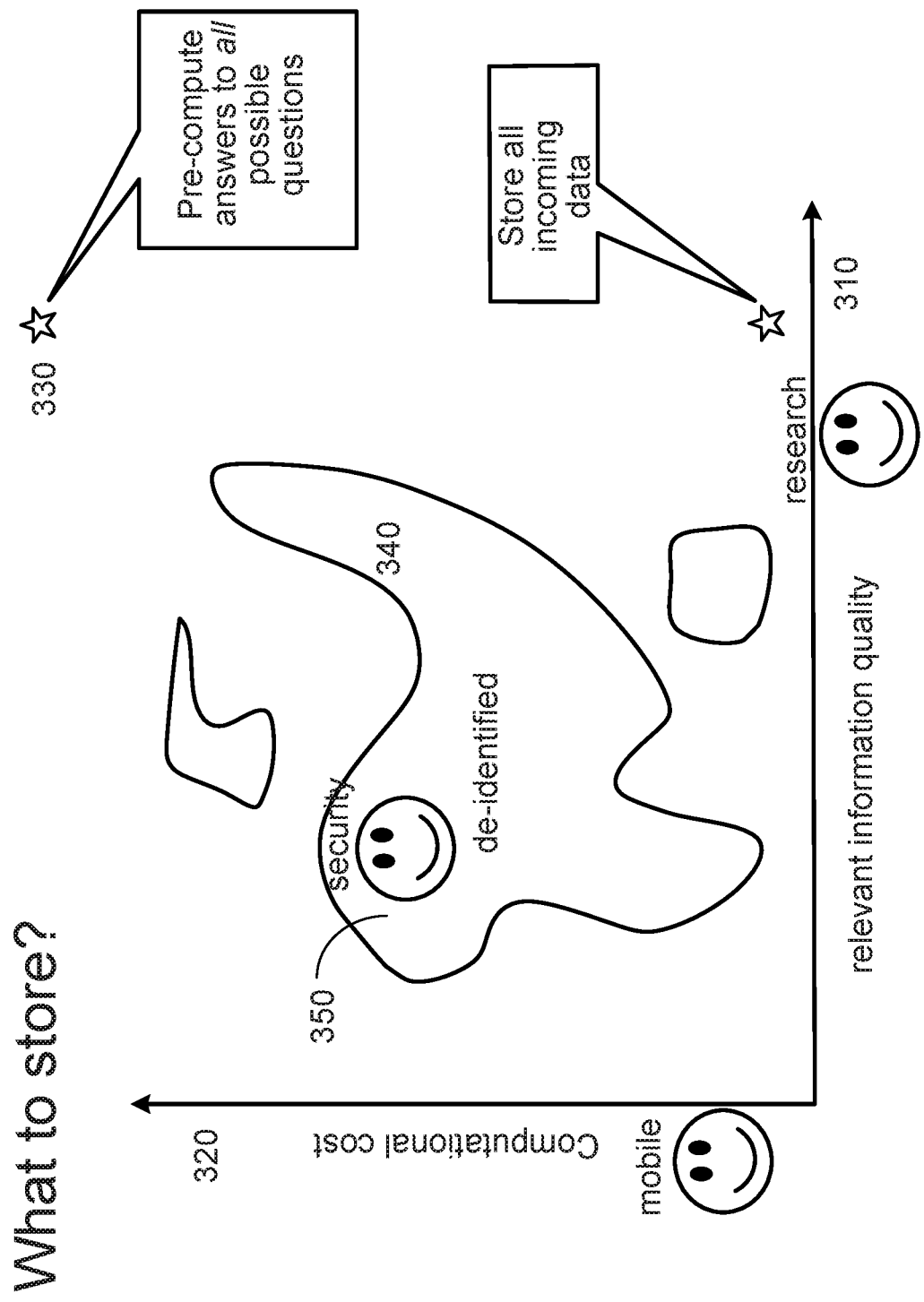
FIG. 2 is a graph depicting a relationship between computational cost and relevant information quality for various combinations of stored information in accordance with an exemplary embodiment of the invention.

Referring next to FIG. 2, in one embodiment of the present disclosure, the user, other individual, or automated process may make a determination as to which level of security will be employed, and if a version such as 130 is selected from FIG. 1, a determination of the amount of information and generic data that is to be stored must be made. As noted with respect to FIG. 1, in addition to addressing the ability to currently process information based upon available processing power, and the ability to provide security to images that cannot be reconstituted to determine identity. Thus, it is preferable in accordance with an embodiment of the present disclosure to store enough data that future analysis and processing on the feature data is possible while providing sufficient security to protect the identity of any individual included in an image.

As is therefore shown in FIG. 2, similar to graph 100 in FIG. 1, on the "x" axis 310 is the storage of information, with the far right equating with storing complete images (i.e. all of the data). The "y" axis 320 describes computational cost of processing data. In a situation where all images were stored, but they cannot be stored indefinitely (for example), ideal data processing would take place at point 330, where the answers to all possible questions were pre-calculated, before deleting of the data. Not only is this quite computationally expensive, it is also not possible to know each and every question ahead of time. Area 340 on the chart identifies a selection of information where the stored information (features) result in de-identified, secure information, but where in the future, this information may still be processed in order to provide additional insight as requested. Any data storage configuration 350 residing in area 340 will meet these criteria. Therefore, in accordance with a preferred embodiment of the present disclosure, the proper number of features to be stored is determined, data is stored using these features, and then in the future, additional processing may be performed on the stored data. As noted, the location of configuration 350 may be determined by a user or in accordance with an automated process or other testing.

Such testing or processing may provide one or more guidelines as to the number of features to be extracted from one or more images and to be stored in order to support any future processing. The images to be processed may be further classified by complexity or the like to determine the number and type of features to be extracted (i.e. more complex images may result in more features to be extracted, representing the richness of information available, while less complex images may only warrant extraction of a fewer number of features). Once such classifications are determined, they may similarly be used to classify and process future images in a more streamlined process. Thus, for images of certain complexity, features determined to be helpful in the processing of prior images including a similar complexity may again be used. Alternatively, testing may be performed during live processing on each image, or on a subset of images, to adjust on the fly the number and type of features to be extracted.

As noted with respect to FIG. 2, in addition to addressing the ability to currently process information based upon available processing power, and the ability to provide security to images that cannot be reconstituted to determine identity, the subject matter of the present disclosure relates to systems in which the feature or other data stored in accordance with the selection of features to be stored for each image allows for the future processing of image data without maintaining the actual complete image. Thus, as described above, in a situation where the feature data is stored and the full image is deleted, it is preferable in accordance with the present disclosure to store enough data that future analysis and processing on the feature data is possible. In such a manner, image data may be stored in a secure, de-identified manner, but also allowing for the ability to reprocess the data in the future should new analysis methods be developed, or should different questions be asked of the data.

In an alternative embodiment of the present disclosure, rather than predetermining a number of features to be extracted from an image, or making such determination in an automated fashion during processing of an image, a mechanism for determining a number of features/generic layers to be extracted may be provided to a user, such as a slider, dial, or number selector. Thus, the user may be provided with a visual mechanism for selecting the relationship between security and level of information. For each image or each batch of images, based upon the subject matter thereof, the user is able to select the number of features stored, and thus the tradeoff between security and data availability. The system may preferably determine a most useful set of stored features, or a level of granularity may be provided to users to identify any desired bias in the selection of such features. For example, if the user is likely to want to answer questions in the future focusing on a particular area, features may be chosen that are more likely to help in answering such questions.

In accordance with a preferred embodiment of the present disclosure, various processing may be performed on the one or more images to identify one or more features of the subject of the image. In a more preferred embodiment, the subject may be the face of a person, and the features may comprise one or more keypoints or landmarks, and may further comprise one or more known predetermined and mapped keypoints or landmark points, or time-domain features such as significant activities. Alternatively, such features may be determined through analysis employing an unsupervised learning process, a supervised learning process, or other teaching or learning process.

It should be noted that the ability to process these features, including one or more keypoints or landmark points may be limited by the available processing power of the associated computer processor. Thus, for example, while a processor associated with a mobile device may be able to extract "x" features or points, a dedicated processor may be able to extract 10×, 100× or more features or points. Therefore, it is important that any processing system be able to address these varying number of points.

Figure 3:
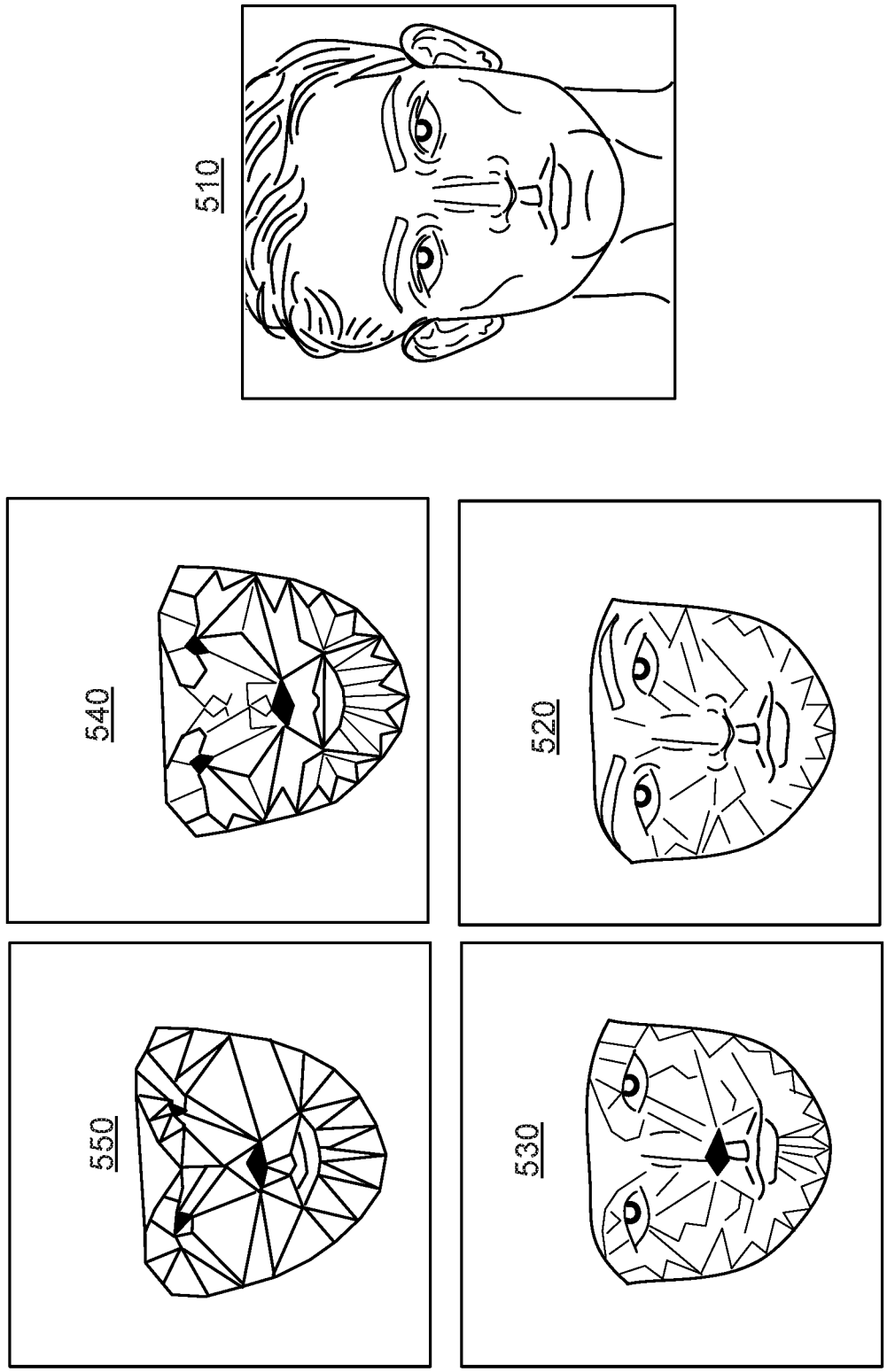
FIG. 3 depicts various levels of keypoint de-identification in accordance with an exemplary embodiment of the invention.

Referring next to FIG. 3, an exemplary embodiment of the present disclosure is shown. In FIG. 3, an initial image of an individual 510 may be captured by a camera or other image capture device, whether as a stand-alone image, or as an image as part of a sequence of images, such as in a video. As is evident from FIG. 3, when reviewing image 510, it is possible to determine the identity of the subject. Image 520 is a post-processing image derived from image 510, and includes a high number of extracted features, or in this case keypoints or landmark points. By no longer storing the complete image data, but rather storing a set of these points, data storage requirements can be greatly reduced. Additionally, such pre-processing may allow for faster computations when further processing the data. As can be seen from image 520, however, it is still possible to determine the identity of the person originally shown in image 510.

Moving next to image 530, another post-processing image derived from image 510 is shown. The number of points stored associated with the image has been reduced from the number shown in image 520. As can be seen, while the major features are still visible, some of the identifying detail has been removed. It may still, however, be possible to identify the individual in image 510 by looking at image 530. Additionally, with further computer processing, it may be possible to regenerate something approximating image 510 from image 530.

Fewer points are stored and used to generate image 540, and indeed, one can see that the ability to determine the identity of the subject in the image is reduced. Image 550 relies on even fewer points, and may be considered de-identified, as there is not enough stored information to go back to the image 510.

It is important to note that the points stored in image 550 are preferably a subset of the points stored in image 540, which are a subset of points in image 530, and then 520. Alternatively, and more generally, a relationship of some sort is preferably defined between the keypoints/features in the different images. By determining the most critical points for determining action, recognition or the like, these points can be prioritized in image 550, but also stored in images 540, 530 and 520 to allow for consistency of processing.

As noted, in a situation where different numbers of features or points are extracted, the fewer points are preferably a subset of the extracted larger number of points. Thus, when processing is to proceed, it is possible to combine images having a different number of extracted points. Processing may be variable based upon the number of points, or may be based upon the minimum number of points in one of the images to be processed, these same minimum number of points being processed from each stored set of points representative of an image, and irrespective of whether additional points may be available for processing.

As described with reference to FIG. 3 (and also considering FIG. 2), in the event that a very large number of points are extracted from an image (i.e. image 520), it is possible to maintain a high quantity of relevant information. While ideal for potential future processing, this situation also results in maintenance of the identity of the subject of the image. On the other hand, if only a few points are extracted (i.e. image 550) it is less likely that the identity of the person can be reconstructed. In accordance with a preferred embodiment of the present disclosure, a predetermined number of features may be preferably identified that allow for future processing of data, but result in a lossy dataset so that the identity of a subject in an image cannot be determined, and the information necessary to do so is not recoverable. By properly selecting the correct number and universe of points to be extracted, a balance between information (and thus future ability to reprocess the visual information), and security (having lost enough data to not allow identity to be revealed) may be achieved. While FIG. 3 depicts selecting features and points from a face, extracting such features from a hand, other body part, or any other portion of a scene of an image may be employed.

Thus, the selection of the number of types of features, or points to be selected may be performed in a simple manner (i.e. limiting to a particular predefined subset of points to be extracted), or may be performed in a more complex iterative manner, such as by evaluating the ability to reconstitute information given a set of features, and then adjusting whether to extract a greater or fewer number of points, or even whether to extract different points, regardless of the number of points. Additionally, various external information may be used in order to guide in point selection. For example, if a particular population is included, this may result in particular keypoints and features being selected. For instance, if a patient population has an issue with facial twitching, then in accordance with a preferred embodiment of the present disclosure, features selected may be one or more that allow for an in-depth analysis of any twitching on the face. Other desired features may also be employed in order to extract particular information for use in a particular analysis.

In addition to selecting one or more keypoints or other features in the visible spectrum, non-visible light, or other areas on the electromagnetic spectrum may preferably be employed. The use of such non-visible and other electromagnetic radiation allows for the extraction of additional information from an image, and for example the face of a person in an image. It is also contemplated in accordance with one or more embodiments of the present disclosure that different features or other keypoints may be selected in accordance with the different forms of electromagnetic radiation. Various information and analysis may be performed in accordance with each of these multiple forms of radiation, the results thereof interacting to provide yet additional information in determining one or more features. Various computational photography techniques may be employed, utilizing so called "edge of camera spectrum" to formulate a greater and much higher resolution understanding of, for example, blood flow and blood pressure. Such computational photography techniques can thus be utilized to build upon derivative data sets. Indeed, any applicable features may be employed, either alone or in combination, to extract valuable data.

In accordance with one or more embodiments of the present disclosure, it is anticipated that the use of one or more sections of the electromagnetic spectrum will allow for an in-depth analysis of facial or other visible user features. For example, rather than simply noting external facial features, use of the techniques and systems disclosed herein allow for the determination of the location of various blood vessels under the skin of a user in the field of view of a camera. Over time, differences determined in the various images provide information about the performance of the user, and may further indicate changes in disease, physical ability, or the like. Such changes, for example, may be more visible under near-infrared light, or other wavelength of energy, thus resulting in additional information being extracted based upon the use of multiple types of light, energy, or other data extraction mechanisms.

Thus, by overlaying multiple layers of information, irrespective of the amount of information provided in each of those layers, a more concrete picture of the status of an individual may be provided. Information collected from lower power devices may include lower resolution information, such as images with fewer pixels, or may include different mechanisms for data collection. As more information is acquired, either through different collection mechanisms, or as the power of collection improves over time, correlations between collected data and negative outcomes (or positive outcomes) in one or more medical therapeutic areas may be provided. The system may therefore be employed as a diagnostic tool for predicting disease or other diagnosis based upon processing of visual images of a user. By allowing for the use of such varied layers, the system is robust to methods of collection, timing of collection, and storage formats of the information, thus "future proofing" the system to rely on older data (perhaps at lower resolutions), and newer collected data, having a higher resolution, or a newer or new data collection technique.

Figure 4:
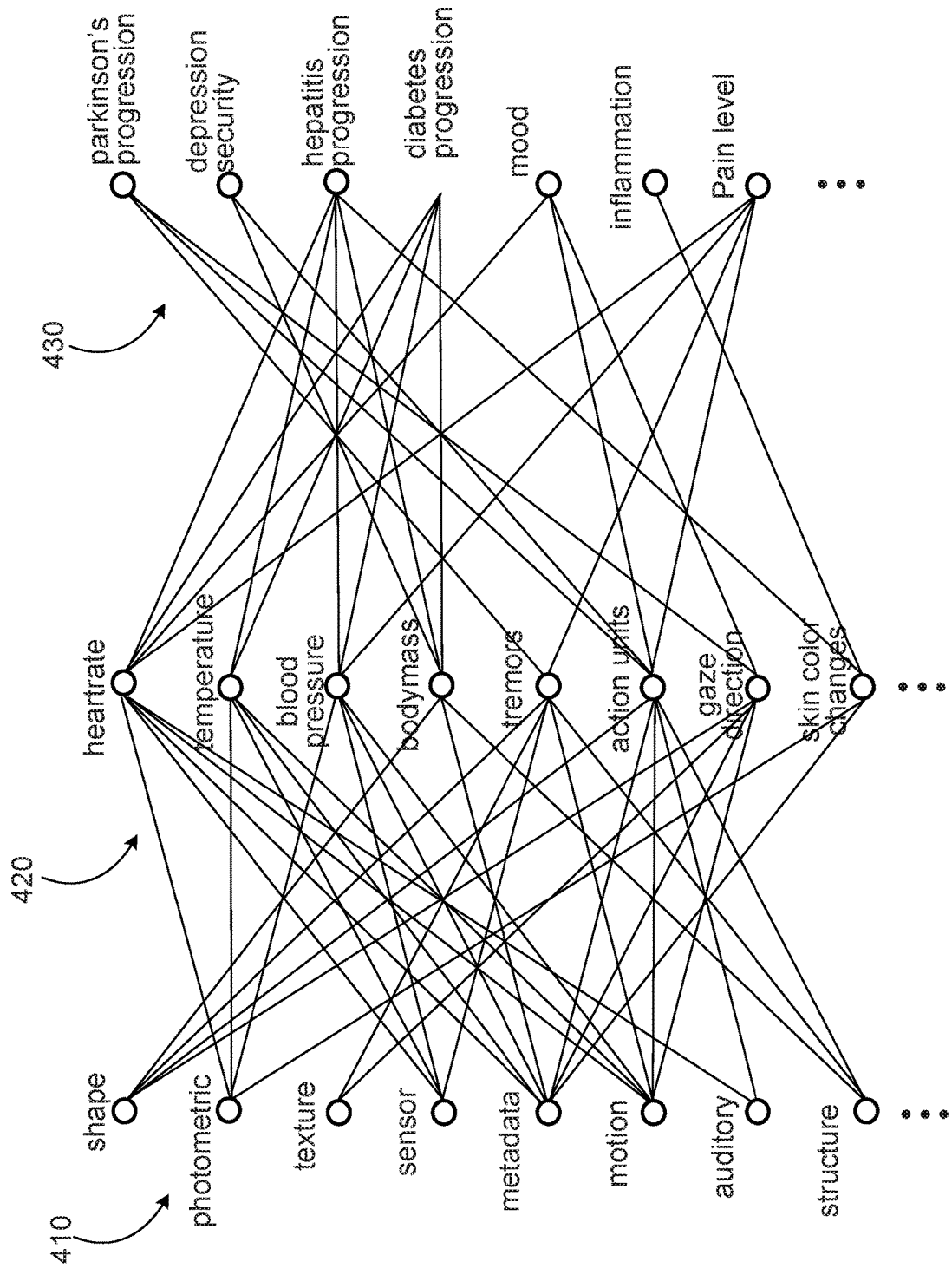
FIG. 4 depicts a relationship between various sensors, measurements and disease determinations in accordance with an exemplary embodiment of the invention.

As is shown in FIG. 4, any number of sensors 410 (in addition to visual sensors) may be provided to collect corresponding pieces of information. As is shown in the exemplary embodiment shown in FIG. 4, one or more of such sensors may, without limitation and by way of example only, measure one or more layers/features, such as shape, light reflection (photometric), texture, other generic sensor, metadata, motion, auditory information, structure, etc. The use of these inputs, combined in different manners, results in the ability to determine one or more conditions/quantities 420, including, without limitation and by way of example only, heartrate, temperature, blood pressure, body mass, tremors, action units, gaze direction, skin color changes, etc. These conditions/quantities 420 may in turn be combined in order to diagnose one or more conditions, including, without limitation and by way of example only, Parkinson's progression, depression severity, hepatitis progression, diabetes progression, mood, inflammation, pain level, etc.

Processing included in FIG. 4 may be utilized to explore potential diagnosis 430 upon measurement of information from sensors 410, or may separately be utilized to identify an expected potential diagnosis 430, and in turn determine which conditions/quantities must be measured to confirm the diagnosis, and in turn which sensors 410 must be used to measure appropriate input information to confirm the conditions quantities. Thus, the system may be employed to measure multitude of quantities, and in turn, determine a diagnosis (moving from left to right in FIG. 4), or may be employed to confirm a diagnosis, thus requiring measurement of only the critical conditions and information (moving from right to left in FIG. 4). Therefore, in accordance with the embodiment of the present disclosure noted in FIG. 4, one or more sensor information may be selected to be stored in order to allow for the answering of future questions.

Therefore, in accordance with the embodiment of the present disclosure noted in FIG. 4, one or more sensor information may be selected to be stored (See FIG. 2) in order to allow for the answering of future questions while avoiding the storage of any identifying information. Through the proper selection of conditions/quantities to be measured, this information may be stored while avoiding storing all visual information of an image, or from one or more other sensors.

In accordance with an embodiment of the present disclosure, a user may be monitored performing one or more activities, such activities having been determined to be indicative of existence or progression of disease. Thus, by monitoring a user in accordance with a visual record, or other non-visual record, one or more characteristics may be monitored to determine whether a particular user may be diagnosed with a disease, or whether a user with a particular disease has one or more characteristics that are progressing over time, indicative of a progression of disease.

Figure 17:
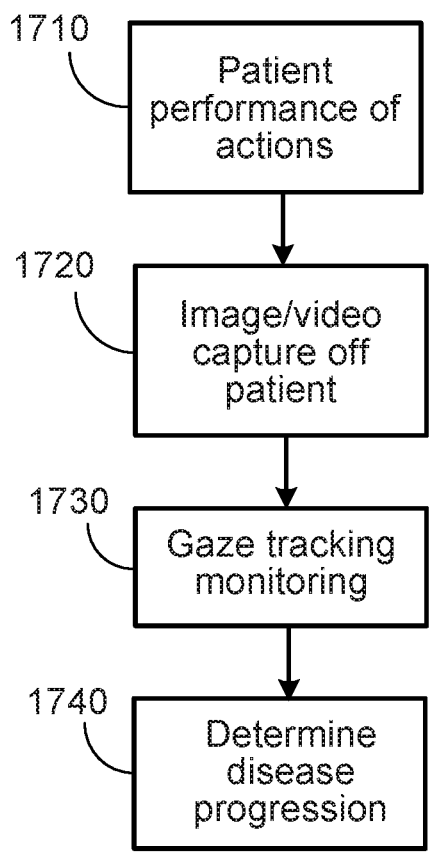
FIG. 17 is a flowchart diagram depicting additional details of an exemplary implementation of monitoring to determine disease progression.

Such monitoring may take place in an active or passive monitoring situation. In an active monitoring situation, as is shown in FIG. 17, the user may be asked to perform a particular set of actions, and is preferably led through these actions on a mobile or other local device at step 1710. A display associated with the local device displays one or more instructions to the user, and then captures (visual, audio, etc.) information related to the performance of the actions by the user at step 1720. Thus, if the user is to perform an eye movement test, the user may be instructed to watch a marker on a display, for example. Such a marker may then be displayed on the display, and moved in a predetermined sequence around the display. This feature thus measures ability to maintain focus on a single item moving through a field of view. Monitoring or eye movement ("gaze tracking") may be employed at step 1730 to determine disease, or if performed over time, may be employed to determine progression of disease as is shown at step 1740.

In an alternative embodiment, a user may be asked to focus on a particular marker on the display at step 1710, and a second marker may be provided on the display, and the ability for the user to continue to focus on the initial marker may be measured at step 1730. This feature thus measures ability to maintain focus, and how easily the user is distracted. Again, monitoring over time allows for a determination of progression of disease at step 1740.

In a still further embodiment, the user may be monitored without providing a particular stimulus on the display. For example, the ability for a user to consistently read text on a screen, or otherwise focus on items in the world around them may further be monitored in a passive manner.

In yet another embodiment, an augmented reality or virtual reality scene may be presented to a user, and a response to the presented information may be monitored. Such an augmented or virtual reality schema may be employed with either active or passive monitoring situation, and may preferably be employed when encouraging a user to follow one or more steps associated with monitoring and encouraging proper medication administration. (see one or more of U.S. Pat. Nos. 8,731,856, 8,731,961, 8,666,781, 9,454,645, and 9,183,601 patents previously incorporated herein by reference). The augmented reality system may similarly be employed to provide one or more instructions or other guidance as noted in these applications incorporated by reference, and may further, after analysis of collected visual or other data, be used to provide additional instructions to the user to properly perform one or more desired sequences, such as properly administering medication, in response to determination of an error. The system may be applicable to oral, inhalable, injectable, or any other method of medication administrations, or other actions associated with health or health status.

Movement may also be tracked, and similarly may be tracked both actively and passively. Active monitoring may ask the user to perform a predetermined sequence of steps, and confirm proper performance, and changes in ability of performance over time. Similarly, passive monitoring may track gait changes over time, ability to stay seated without fidgeting, etc. The monitoring of either of these movement issues may be employed to diagnose or monitor progression of disease.

Additionally, making reference to U.S. Pat. Ser. No. 13/189,518, previously incorporated herein by reference, output from any of the schema for presenting and monitoring a user may be input into a system for determining current and potential future medication adherence status of a user. Therefore, any of the features of the present disclosure may be employed as inputs into the system as described in the '518 application, allowing for a more robust set of inputs to drive determinations of adherence and health status, and to drive potential interventions, monitoring and the like of any particular user.

The following additional features, parameters or characteristics may be actively tracked in accordance with one or more embodiments of the present disclosure: observe reactions while performing task; Track point; Look at pictures of emotional faces; Coordination test; Balance test; Reaction speed test; Reflex/reflex suppression; Memory; Keeping appointments (engage with phone at designated time); etc.

The following additional features, parameters or characteristics may be passively tracked in accordance with one or more embodiments of the present disclosure: observe reactions while engaged in other activities (Gaze; Action units; Head motion/pose; Pupil dilation; etc.)

In a further embodiment of the present disclosure, when administering or performing a therapeutic or recovery exercise, the following additional features, parameters or characteristics may be actively tracked in accordance with one or more embodiments of the present disclosure: Tracking motion; Concentration; Memory; ability to focus one's eyes (e.g. after eye surgery to monitor healing timeline). Remote therapy may also be incorporated when administering or performing a remote therapeutic or recovery exercise, or during passive monitoring of patients remotely: administering therapeutic/recovery exercises with remote guidance: Track markers while conversing; Symptom tracking; Tremors; Involuntary motions; Jaundice; Temperature; Heart rate; BMI. Recovery tracking may also review one or more of Recovery tracking; Skin/cosmetic surgery; Eye surgery (pupil size etc.), Hair implant, etc. Of course, other characteristics may also be monitored to the extent that these characteristics are determined to be indicative of diagnosis or progression of disease.

Furthermore, to the extent any such relationship between a measure characteristic and disease has not yet been defined, in accordance with an alternative embodiment of the present disclosure, collected data may be processed to determine any such relationships to allow for use in the future. Different demographic groups may be employed to determine characteristics in these particular demographic groups, and thus allow for targeted diagnosis and monitoring of disease. The use of supervised or unsupervised learning techniques may be employed to analyze such data to determine any applicable relationships.

Figure 5:
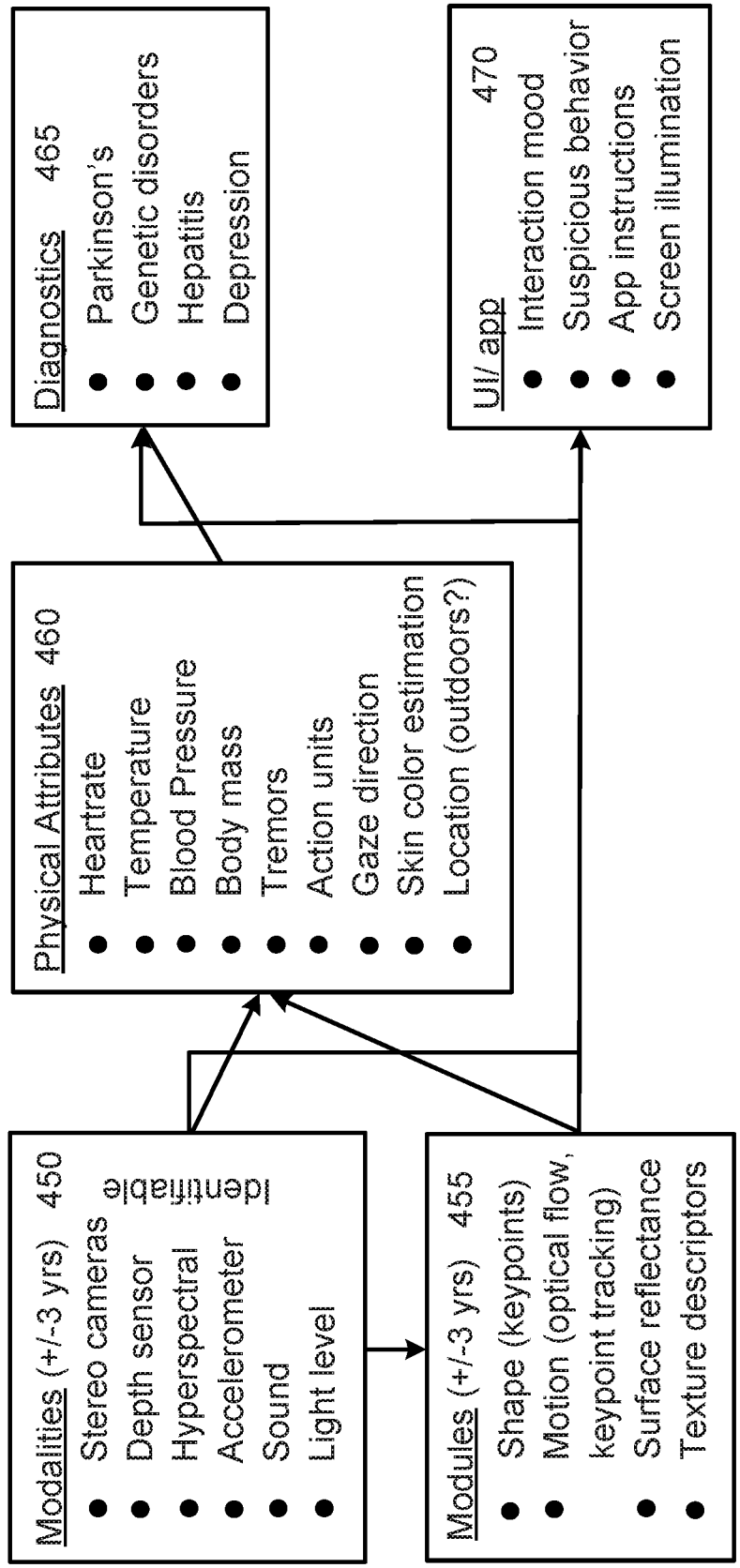
FIG. 5 depicts an additional relationship between the items depicted in FIG. 4, and in particular physical implementation of one or more of the relationships thereof.

Referring next to FIG. 5, an additional view of the structure presented in FIG. 4 is shown. As is shown in FIG. 5 in addition to FIG. 4, sensors 410 may take on any number of modalities 450 or modules 455. Modalities 450 collect identifiable information while modules collect non-identifiable information. A combination of this collected information preferably triggers a confirmation of one or more changes in the noted one or more physical attributes 460, ultimately resulting in an output of a potential diagnosis 465. Analysis of one or more of modules 455 may also provide one or more outputs to a user-facing output, such as a dashboard or mobile app, related to analysis of the modules 455, thus predicting one or more of, for example without limitation, interaction mood, suspicious behavior, instructions (that may be required to assist the user), or screen illumination (which may be employed in the event of a dark room where video cannot otherwise be collected).

By dividing populations by demographics, disease state, or other mechanism, it is also desirable to provide input into the system as to one or more medical or other conditions that may be more likely or more dangerous in the identified population. While older individuals may be more likely to suffer a stroke, for example, younger individuals may be more prone to overuse injuries, or other disease states. By providing such information as an input to the system, a reduced set of disease states or other changes in parameters may be examined, thus improving the accuracy, repeatability and precision of the inventive system. Desired sensors may be employed in order to watch for a particular disease state, or other indication of disease of a user.

Any such readings determined in accordance with the inventive system may also be correlated with one or more known, validated scales or question sets. Correlations between responses to the scales and feature determination may be provided, resulting in yet additional predictive analytics, and less reliance on the actual scales going forward. Thus, in accordance with FIG. 4, one or more combination of sensor input data may be determined to be useful in identifying a particular condition. Once value ranges for each of the desired sensor inputs are determined that correspond, as a whole, to a determination of existence of a particular diagnosis, this combination of sensor input and data value ranges may be stored for future use.

Once various feature sets have been determined to have a predictive capability (for predicting, for example, existence of a particular disease, one or more data masks may be generated to allow for a review of incoming future data to similarly determine existence of that same particular disease, for example. Such a data mask may comprise one or more feature values indicative of a state of an individual. Thus, for example, rapid weight gain, an increase in blood pressure, and a change in skin color may be defined as indicative of the progression of a particular disease. By providing such a mask, a simple diagnostic tool may be provided that allows for an immediate and automated determination of potential medical conditions of an individual, and may further indicate a preferred path for addressing these conditions. For example, the individual may be given instruction to rest, to drink fluids, to eat, to call their doctor, to take medication, or to go immediately to an emergency room. The system may further be provided with adjunct systems for performing some of these functions, such as calling a family member, dialing 911 and providing GPS information for location of the individual, and may also provide an initial diagnostic analysis of the health of the individual to those responding to the alert, allowing quicker response and triage on site, or when the individual reached the hospital.

Figure 6:
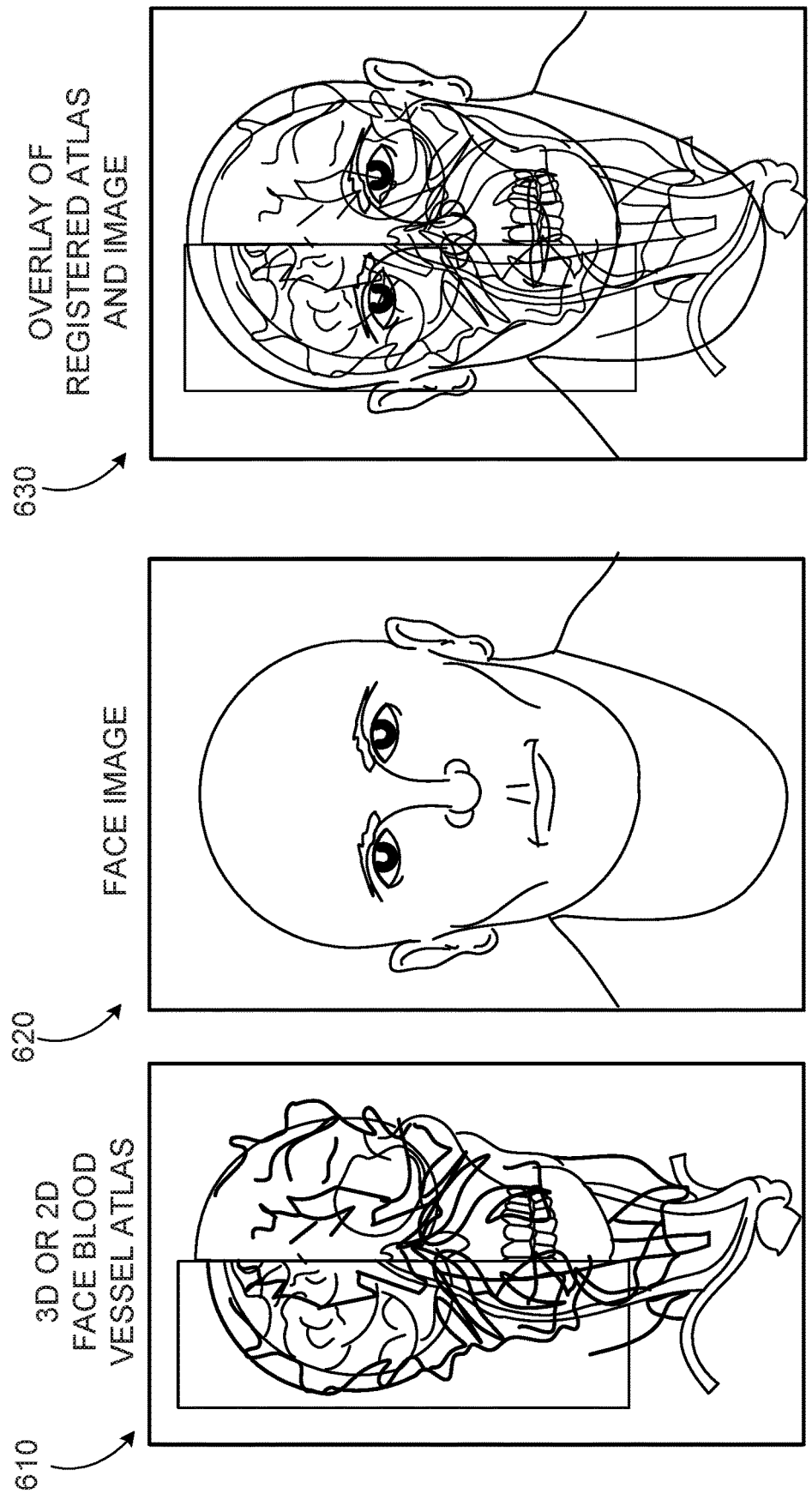
FIG. 6 depicts an exemplary embodiment showing the overlaying of a known physical structure on the face of an individual, thereby improving the ability to recognize one or more physical changes in the physical structure.

By way of example only, understanding the artery, capillary and vein structure of the body may allow for a determination of changes therein, in order to allow for visual measurement of heartrate, temperature, or other bodily measurements, as will be described below with respect to FIG. 6. Thus, in accordance with a further embodiment of the present disclosure, it is possible to focus a visual system on a particular portion of the body of a user to determine visually a heartrate therefrom. As noted above, a system employing visual or other electromagnetic radiation may be employed. It may be difficult, however to determine minimal changes in the skin of a user when the location of such changes is unsure. Thus, the system will be required to scan a complete user body to look for slight changes, and then determine whether these changes are significant to any bodily measurement. Any changes in the collected data may be used to predict changes in health, disease progression, symptom progression, overall health or the like.

As noted by the inventors of the present disclosure, and as a further example, by understanding the artery, capillary and vein structure of the body, determination of changes in any such structure may be more easily determined. By knowing where to look for, by way of example a capillary at the temple of a user, it is easier to determine changes in that capillary as the system can be properly focused, and need not scan the entire body to determine where to look. In order to perform such a task, the inventors of the present disclosure have determined that it is possible to overlay a data mask indicative of the locations of, for example, arteries and veins on a typical face, on an image of an individual. As is shown in FIG. 6, a known face blood vessel atlas 610 may be determined from one or more known data sources. Such an atlas may alternatively be generated in accordance with one or more scans of actual bodies, or any other composite image from which a blood vessel structure can be determined. Overlaying face blood vessel atlas 610 on a face image 620 results in the composite image 630. Referring to such composite image 630, the system may be guided where to look for a particular blood vessel, and any changes thereto. In an additional embodiment of the present disclosure, a plurality of masks may be determined as a subset of the complete mask, based upon desired locations for a particular disease state, or the like. Thus, preferably such mask may be determined after processing data for multiple individuals, and may be categorized by demographics, disease state or the like. The mask may be further customized to a particular individual, and then monitored over time to determine changes in the individual, related to relevant variables, over time. Such changes may be used to predict changes in health, disease progression, symptom progression, overall health or the like.

Figure 7:
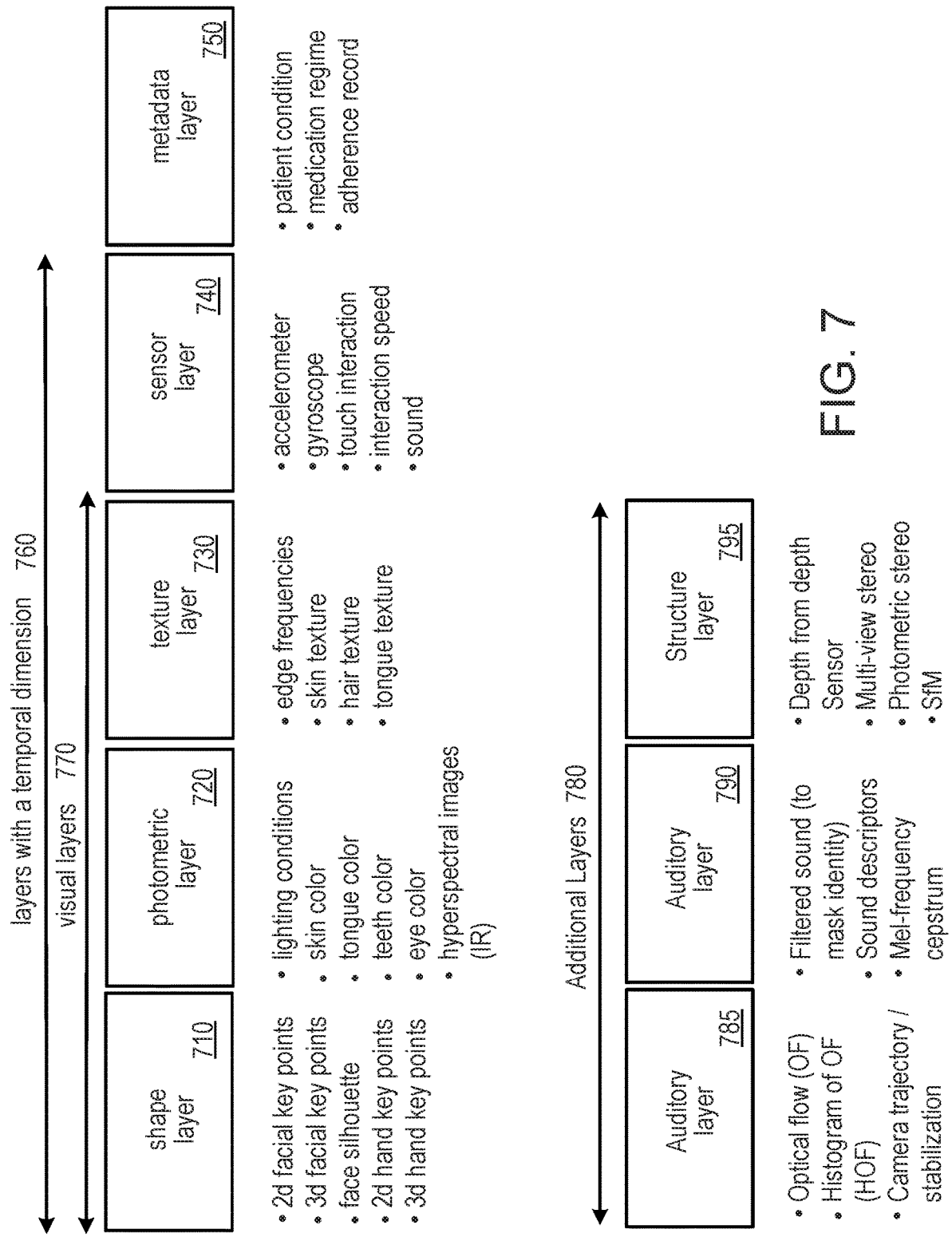
FIG. 7 depicts a structure for feature extraction on multiple sensed layers in accordance with an exemplary embodiment of the invention.

In accordance with a preferred embodiment of the present disclosure, one or more particular facial or other features may be captured from images in question. As is shown in FIG. 7, feature extraction may take place on features captured in visual layers, additionally features captured having a temporal dimension, or using other layers. FIG. 7 describes a set of potential features, or other image elements that may be used to extract information from one or more video or still images. As is shown in FIG. 7, a number of different layers may be analyzed in order to determine one or more features of an image that may be used to store extracted information. These layers may comprise, for example, a shape layer 710, a photometric layer 720, a textual layer 730, a sensor layer 740, and a metadata layer 750. The first four of these elements (710-740) include a temporal dimension 760, while the first three (710-730) additionally include a visual layer 770. Additional layers 780 may further comprise a motion layer 785, an auditory layer 790, and a structure layer 795. For each such layer, various features may be investigated as to whether they are relevant to a particular set of images. For example, if an image has varied lighting conditions, then the photometric layer and lighting conditions therein may be used to store information about an image. If, however, lighting is constant, then this layer and feature will likely store very little information about the image, and may not be used.

The layers of FIG. 7 may be used in a number of different ways. First, one or more of the particular layers may be chosen based upon the desired question to be answered, related to the task at hand. For example, if one desires to identify Jaundice, or other skin discolorations, then the visual color layer may be an important one that should be analyzed, while shape features are likely less important. Identification of tremors, on the other hand, may rely on shape information much more heavily than color. Similarly, the determination of body mass index may rely on shape features, and changes thereto over time. The above-noted various forms of electromagnetic radiation may similarly be employed to allow for additional of these layers to be determined. Thus, for example, shape or color may appear differently employing these different forms of electromagnetic radiation. Additionally, reflectivity or other characteristics of the human body may be measured in response to these different applications of electromagnetic radiation, allowing for additional and varied information to be collected. Audio pulses or the like may be employed, to determine water and/or fat content, as well as any other determinable feature. Additionally, one can extract features from any number of the noted or other layers, and make a determination of whether this information is valuable. For example, extracting color data only to find that the screen is completely black will not result in much information (but may indicate that the system has improperly recorded information). Noting that lighting conditions are consistent is also relevant information, and may or may not be important depending on the task at hand. Therefore, in accordance with various embodiments of the present disclosure, layer data may be extracted, analyzed, and determined whether helpful in a particular situation. Additionally, if one is looking for a particular type of information, the desired layers for analysis may be pre-identified. Any of this information may be reviewed over time to determine, for example, weight gain or loss, blood pressure or pulse change, dehydration, frostbite, hypothermia, or any other measurable quantity. In addition, one or more of the visual layers may take advantage of high speed photography, allowing for the collection of information up to 400 frames per second or higher, for example, to allow further analysis of very subtle changes in skin movement, color, or other micro gestures that may be of interest.

Therefore, in accordance with various embodiments of the present disclosure, layer data may be extracted, analyzed, and determined whether helpful in a particular situation. Additionally, if one is looking for a particular type of information, the desired layers for analysis may be pre-identified. Any of this information may be reviewed over time to determine, for example, weight gain or loss, blood pressure or pulse change, dehydration, frostbite, hypothermia, or any other measurable quantity. In addition, one or more of the visual layers may take advantage of high speed photography, allowing for the collection of information up to 400 frames per second or higher, for example, do allow further analysis of very subtle changes in skin movement, color, or other micro gestures that may be of interest. Images may be considered in chronological order, or may be considered simultaneously, relying on commonality of structure rather than time. Such processing preferably groups incoming images along one or more dimensions other than chronological. In such a manner, images may be grouped in a manner providing the most information for determining existence of a particular characteristic. Such characteristic may be indicative of existence or progression of disease, or may be relevant to any other measureable quantity or quality of disease or other characteristic. By grouping incoming images along such non-chronological dimensions, as more images are collected, the number of images in each grouping may be increased, thus improving the precision of any processes dependent upon these groupings. Any of the layers shown in FIG. 7, or any other applicable layers may be included as the one or more dimensions, and allow for processing of images in a manner most helpful for determination of image status, and in accordance with a preferred embodiment of the present disclosure, helpful in determining state and progression of disease. Thus, captured layers and dimensions may be related to, for example, skin color, eye movement, body temperature, heart rate, or the like.

Therefore, further in accordance with a preferred embodiment of the present disclosure, the one or more layers (either visual or having a temporal dimension, such as layers working with various non-visual sensors, or even metadata), may be examined to determine whether one or more features thereof is relevant to a particular set of images. Once determined to store important information, these features within a single layer, or across multiple layers may be grouped and selected as a subset of keypoints or other information, in a fashion as noted above, in order to select a subset of the possible information, to allow for storage and processing of the data in the future, but preferably in a lossy manner in order to protect the identity, and reduce the ability to re-identify an image. Of course, this process may also be employed even if an image is to be stored in a lossless manner, or in a lossy manner that still allows for re-identification of information stored therein. In addition to a formal visual layer, it is also to further process additional types of electromagnetic radiation, such as ultraviolet, infrared, etc. In such a manner, it is possible to extract features that may not be visible under electromagnetic radiation in the visual portion of the spectrum, but may be more prominent once other areas of the spectrum are used.

Figure 8:
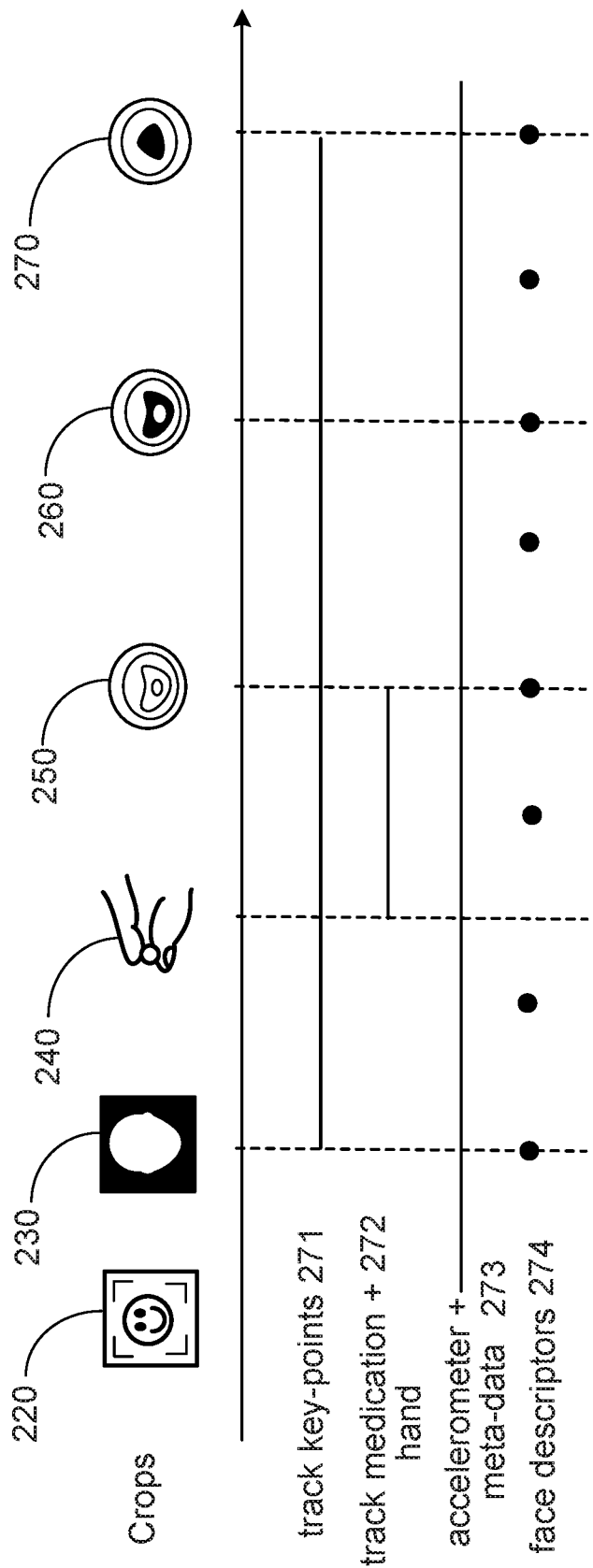
FIG. 8 is an exemplary embodiment of the invention depicting the layers and features that may preferably be extracted when monitoring medication adherence of a user.

Referring next to FIG. 8, a sequence of particular features that may be collected when imaging visual and other information related to determination of whether a particular user has properly administered medication, as noted in the above patents incorporated herein by reference. As is shown in a preferred embodiment of FIG. 8, a number of steps indicative of proper medication administration are shown, including proper positioning of a capture device 210, facial recognition 220, object recognition 230, pill in mouth recognition 240, empty mouth recognition 250 and under tongue empty mouth check 260. As is further shown, in FIG. 8, keypoint tracking 271 may be employed across all steps starting with facial recognition. Tracking keypoints associated with medication in hand 272 preferably takes place only during object recognition 230, while accelerometer data 273 may be used at all times to be sure the capture device is properly positioned. Finally, face descriptors 274 may be employed at any time the face of a user is within the field of view of the capture device.

Such processing may be applied, for example to images of a user administering a pill or film based oral medications, or injectable, inhaler-based, other non-pill based medication, or any other form of patient administration task that may be performed, may be utilized in accordance with one or more of the present disclosures noted in the above-referenced applications. Therefore, in accordance with an embodiment of the present disclosure, a method and apparatus may be provided for analyzing captured patient image data.

The system may process information at a remote system housing the database of collected information. New images acquired by a camera in a local mobile device may be transmitted to the remote location, one or more of the above-noted processing techniques, including extraction of keypoint/feature data may be applied, and then the results of such analysis may be provided as feedback to a user in any number of scenarios. Such keypoint/feature processing data may be used to determine one or more features of medication adherence, facial recognition, facial images, or the like based upon differing levels of stored information and keypoint/feature data. Alternatively, as noted above, processing may be performed in advance of new image acquisition to identify a desired number of keypoints/features to be extracted, and then a system for identifying characteristics of a future image may be provided to the local device to further process acquired images. Such a system may be reduced in processing requirements to allow for appropriate processing on the local mobile device. By providing either of these systems in accordance with a medication monitoring process, when monitoring medication administration, various features of the administration process may be extracted.

A mechanism for determining a number of features to be extracted may be provided to a user, such as a slider, dial, or number selector. Thus, the user may be provided with a visual mechanism for selecting the relationship between security and level of information. For each image or each batch of images, based upon the subject matter thereof, the user is able to select the number of features stored, and thus the tradeoff between security and data availability.

As noted above, in one embodiment of the present disclosure, in a situation where different numbers of features or points are extracted, the fewer points are preferably a subset of the extracted larger number of points/features, as described above. Thus, when processing is to proceed, it is possible to combine images having a different number of extracted points/features. Processing may be variable based upon the number of points, or may be based upon the minimum number of points/features in one of the images to be processed, these same minimum number of points/features being processed from each stored set of points representative of an image.

By way of example, if the selected features are representative of the face of an individual (FIG. 3), images having a small number of points extracted (Image 550) may be representative of the eyes, nose and lips of the subject, as these may provide the most information. Images having a high number of features or points may include these points, and further include points related to forehead, chin, cheeks, etc. (Image 520).

Figure 9:
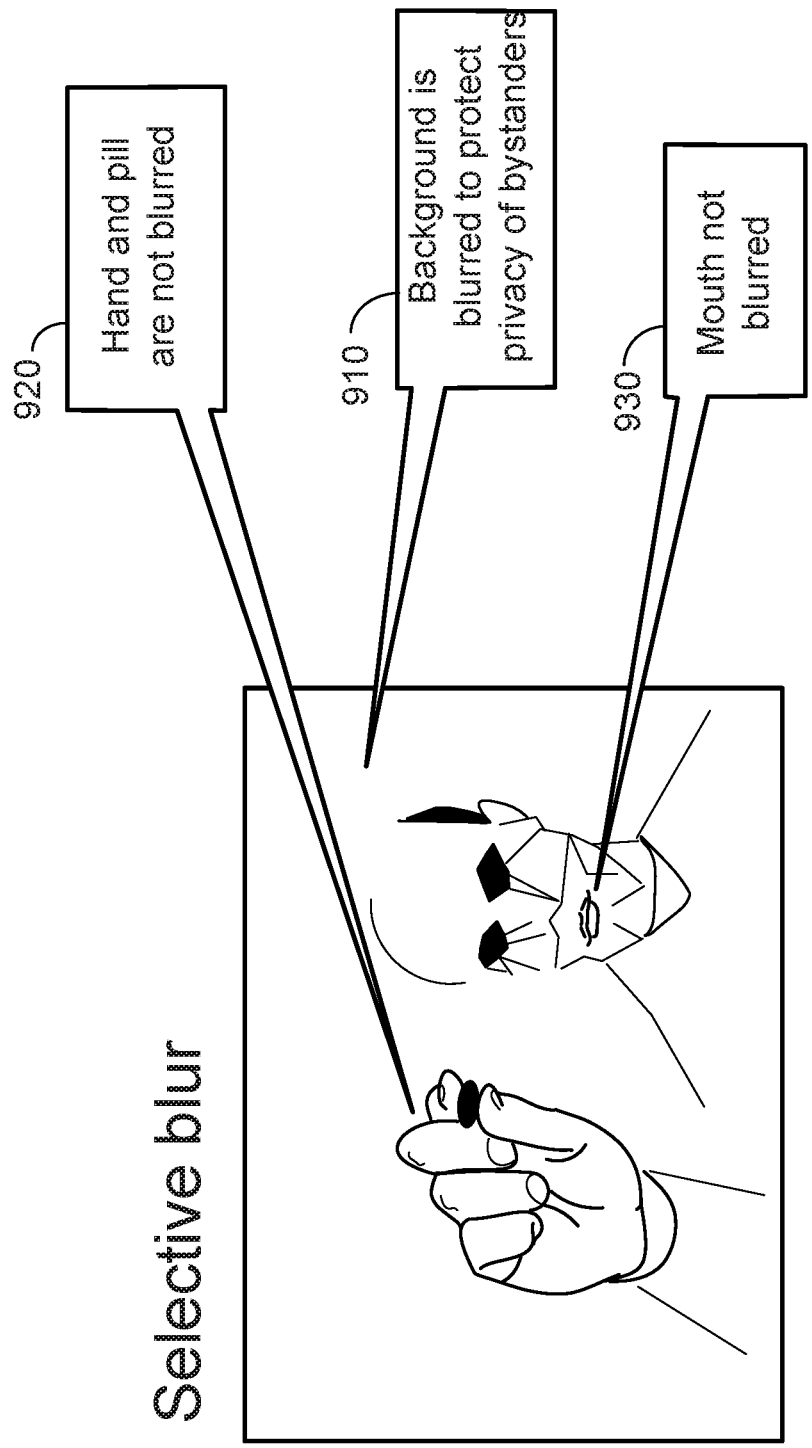
FIG. 9 depicts selective keypoint de-identification in accordance with an exemplary embodiment of the invention.

In U.S. Pat. No. 9,256,776, and U.S. patent application Ser. No. 14/990,389, the contents thereof being incorporated herein by reference, the owners of the present disclosure have described a system that allows for the partial blurring of images to de-identify one or more images in a video sequence. In accordance with the present disclosure, as set forth in FIG. 9, this concept may be combined with the techniques and systems disclosed herein, whereas the unblurred portion 910 of a user's face, for example, may be de-identified further using the keypoint system described above with respect to FIG. 3, while a pill in hand portion 920, or a mouth portion 930 may remain unblurred. In such a manner, additional security provided in that any portion of the image that is not blurred is de-identified, and any portion of the image that is not keypoint de-identified, and likely of less interest to the viewer, is therefore blurred. This is a useful feature to insure that any individual walking through the background of the image is not identified inadvertently.

De-Identification Models

Figure 10:
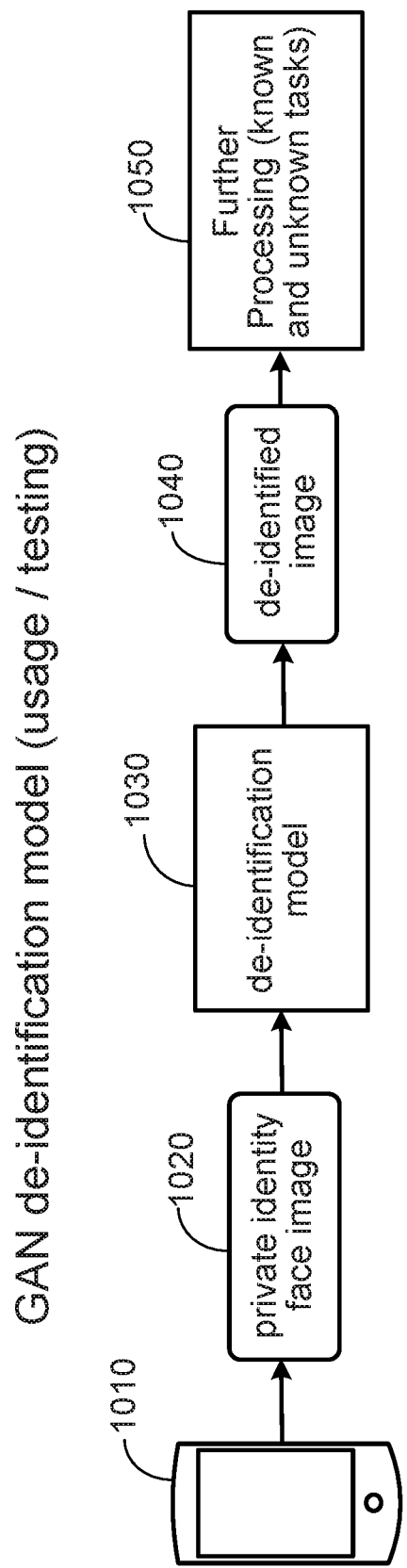
FIG. 10 depicts a de-identification model, including a method for generating de-identified images which are compatible with existing modules, in accordance with an exemplary embodiment of the invention.

Referring next to FIG. 10, a de-identification model, including a method for generating de-identified images which are compatible with one or more existing modules, is presented in accordance with a preferred embodiment of the present disclosure is shown. FIG. 10 describes the process of de-identifying a particular presented image with a trained de-identification model (details about training are presented in FIG. 11).

As is shown in FIG. 10, at step 1010 an image is preferably acquired in accordance with an image acquisition process employing an image capture apparatus, such as a camera, associated with a mobile device, standalone camera, or other image acquisition system. At step 1020 an image of a face is preferably extracted from the acquired image. It is desirable to mask the identity of the face. The facial image is thus preferably passed to a de-identification model at step 1030. The output image at step 1040 comprises a de-identified image which preferably appears as a natural image of a person whose identity is public (i.e. the identity of the facial image has been transferred into an image of someone else whose identity need not be protected, or to a composite facial identity that is not identifiable as any particular individual). The output image at step 1040 will retain aspects deemed important for the tasks (known and unknown) that may be performed (e.g., in a preferred embodiment, layers as noted above will be retained to allow for the answer of future questions) but private characteristics are preferably replaced with public ones. For example, the pose, expression, skin tone and gaze direction of the individual in the private image may be maintained but other private attributes are preferably synthesized in a manner which will prevent identification. The resulting synthesized image therefore includes a natural appearance, and is compatible with existing modules for known (and unknown) tasks which expect a natural face image. Thus, at step 1050, additional processing may be performed on the output image as if the image were that of a simple acquired facial image.

Figure 11:
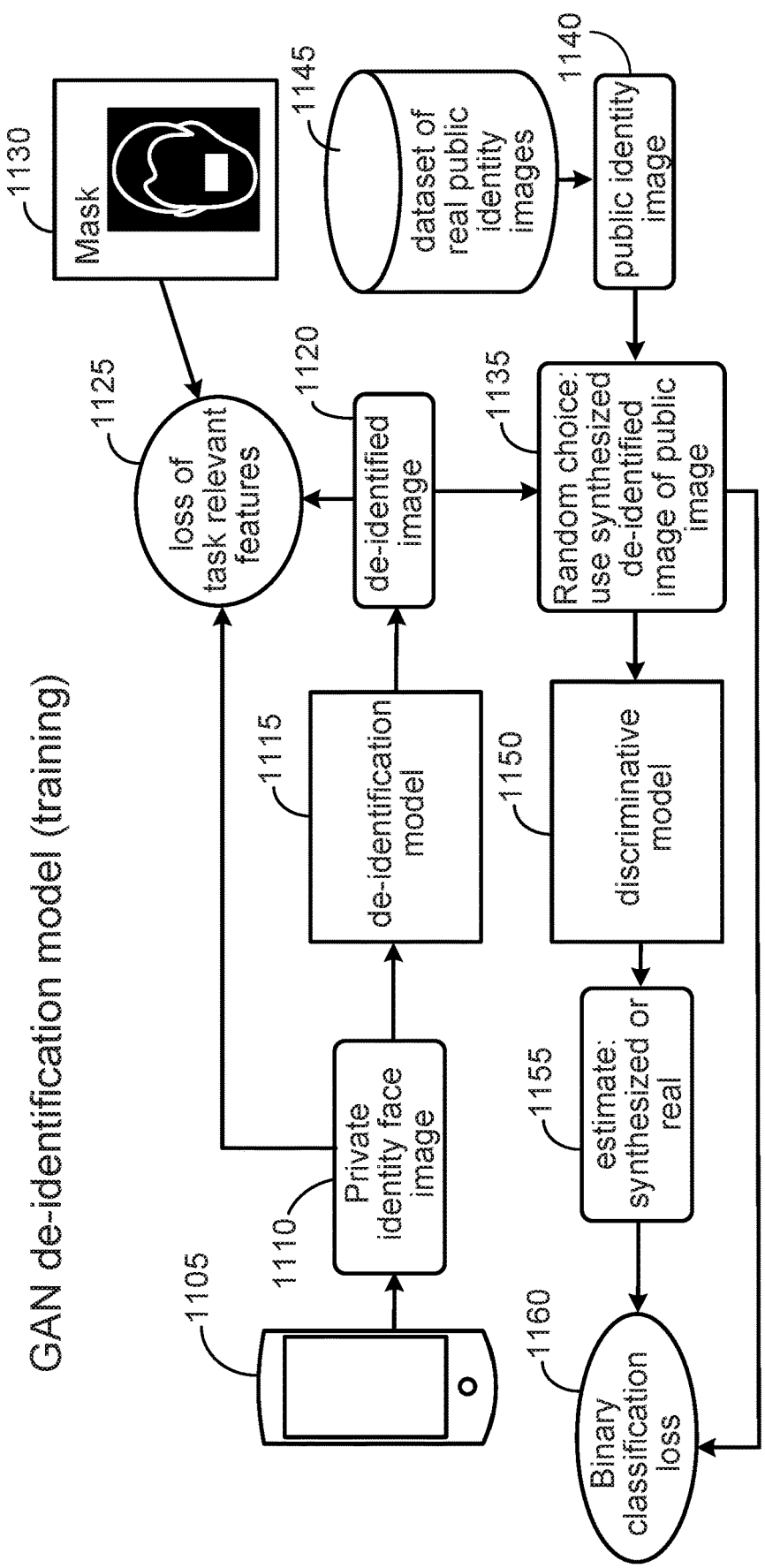
FIG. 11 depicts a method for training the de-identification model of FIG. 10 to optimize the parameters thereof, in accordance with an exemplary embodiment of the invention.

Referring next to FIG. 11, a method for training the system of FIG. 10 to optimize the parameters of the de-identification model is shown. The optimization method preferably follows the processes as described in accordance with a Generative Adversarial Network (Goodfellow, Ian, et al. "Generative adversarial nets." Advances in neural information processing systems. 2014.), and self-regularization (Shrivastava, Ashish, et al. "Learning from Simulated and Unsupervised Images through Adversarial Training." arXiv preprint arXiv:1612.07828 (2016)).

As is further shown in FIG. 11, an image is acquired at step 1105, and at step 1110 a private-identity facial image is extracted therefrom. Next, at step 1115 a de-identification model receives the private-identity facial image and synthesizes a de-identified version of that image at step 1120. The de-identified result at step 1120 is evaluated with two loss functions so that the parameters of the de-identification model are optimized to minimize the loss on a large dataset of training examples. Thus, the de-identification process should not modify task relevant features, so that a greater percentage of future questions can be answered (e.g., in a preferred embodiment, a greater number of layers associated with likely potential questions are preferably retained). A loss function at step 1125 evaluates retention of relevant features in a way appropriate to the task at hand. For example, in order to verify medication ingestion it may be desirable to minimize changes in the mouth area. This loss may be implemented by measuring the distance between the private and de-identified image using a mask 1130 which assigns more weight to differences in the mouth region than to differences in other parts of the image.

The de-identified image at step 1125 may further be combined at step 1135 with a public identity image 1140 (or itself a synthesized image) retrieved from a database or other storage location 1145, and provided to a discriminative model element 1150. This element receives the combined image from step 1135 (which may be a real public identity image or a synthesized de-identified image) and outputs a binary label at step 1155 indicating whether the discriminative model element 1150 has determined that the image is a real or a synthesized image. The de-identification model is trained to generate realistic image which fool the discriminative model. The discriminative model is trained to distinguish between the real and synthesized images.

The discriminator performance is then evaluated in accordance with a calculation of a binary classification loss at step 1160. The results of the discriminator output are compared with the known combination system employed in step 1135 to modify settings in a feedback loop system, as appropriate, until the system can consistently fool the discriminator.

Figure 12:
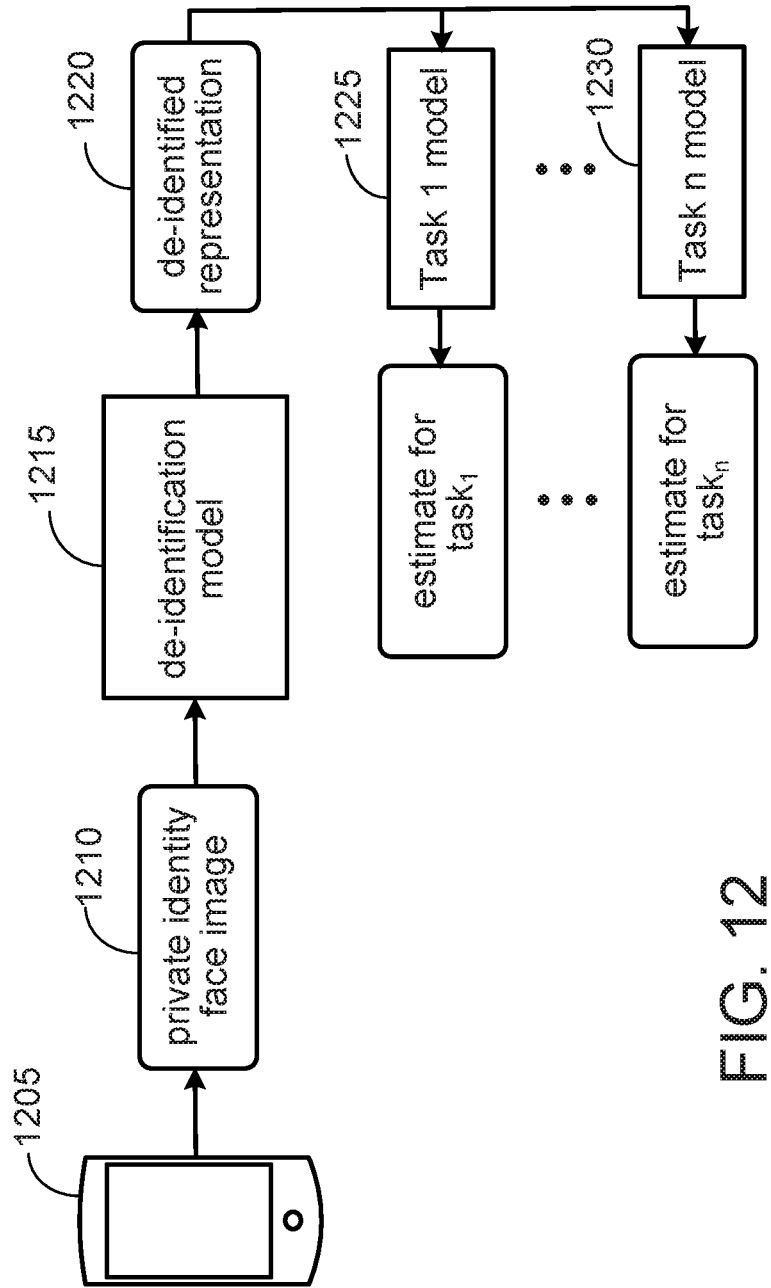
FIG. 12 depicts a joint optimization de-identification model constructed in accordance with an exemplary embodiment of the invention.

Referring next to FIG. 12, a joint optimization de-identification model constructed in accordance with an embodiment of the present disclosure is described. The system and method as depicted in FIG. 12 describes a joint optimization method to generate a de-identified representation of an image which can be used to perform multiple tasks of interest denoted here task_1 . . . task_n. The diagram describes the process of de-identifying with a trained de-identification model (details about training are presented in FIG. 13).

As is shown in FIG. 12, an image is acquired at step 1205, and at step 1210 a face is extracted therefrom, the face including an identity that is desired to be masked. The private image is passed to a de-identification model at step 1215. The output from step 1215 comprises a de-identified representation at step 1220. The output de-identified representation can be used to solve different known tasks, from task model 1 shown at step 1225 to task model n at step 1230. Each of the task models 1 to n preferably rely on one or more layers of information. Thus as noted above, the layers retained in accordance with the selected de-identification model at step 1215 are preferably selected in order to maximize the likelihood of answering one or more future questions. If the representation is trained to provide good performance for a rich and varied set of known tasks it may also be generalizable and useful to other unknown tasks which have some correlation with the known tasks.

Figure 13:
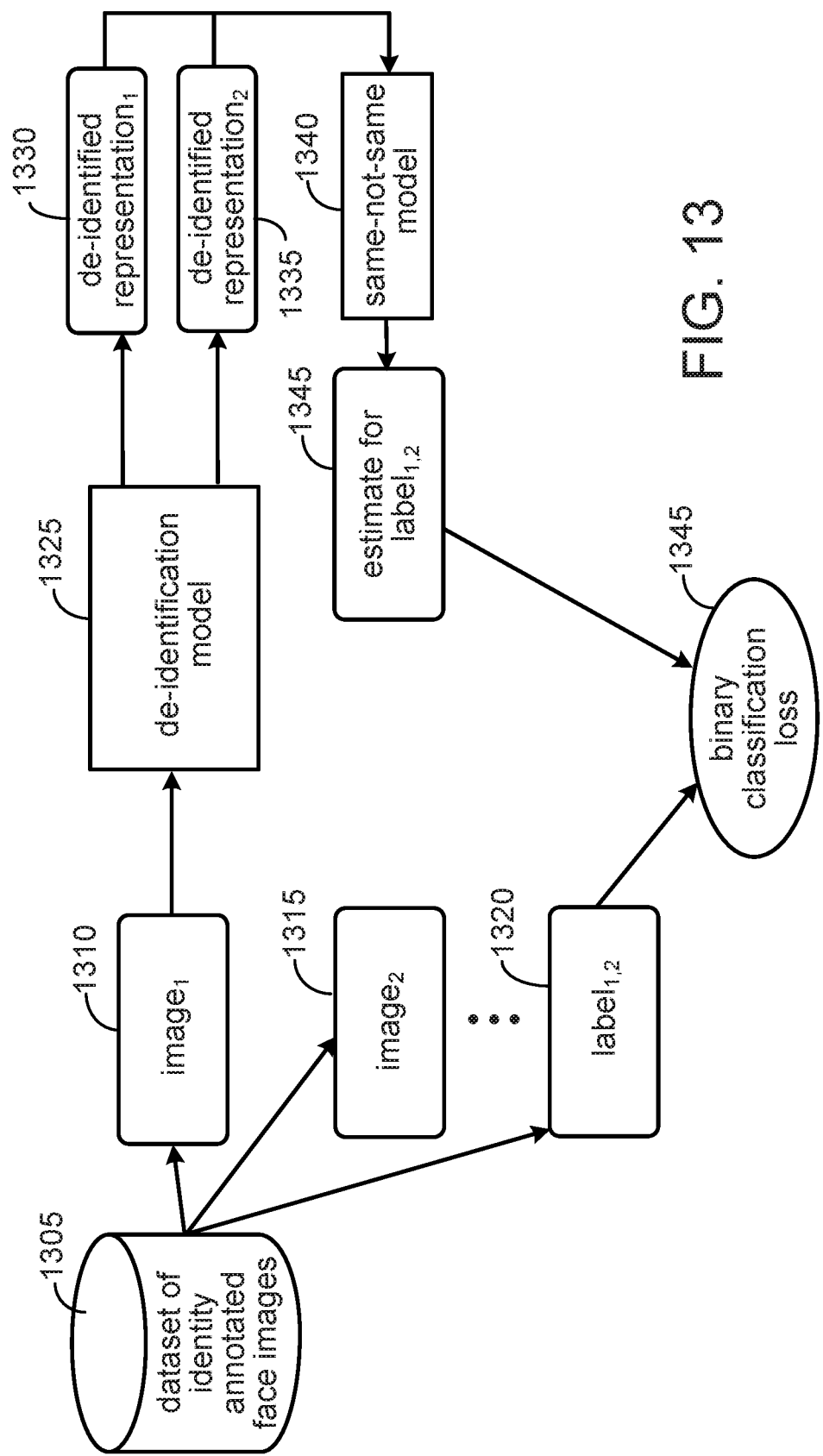
FIG. 13 depicts a joint optimization method for training the joint optimization de-identification model of FIG. 12 to optimize the parameters thereof in accordance with an exemplary embodiment of the invention.

Referring next to FIG. 13, a joint optimization method to train a de-identification model presented in accordance with an embodiment of the present disclosure is described. This method jointly optimizes a number of models in order to minimize a binary classification loss and a sequence of task specific losses. The binary classification loss promotes the de-identification while the task specific losses promote retention of good performance for tasks which rely on the de-identified representation.

A pair of images (image_1 and image_2) with known identities are retrieved from a dataset of identity annotated facial images 1305 at steps 1310 and 1315. At step 1320, a flag is set to indicate whether the images at step 1310 and 1315 are of the same person or not. Next, at step 1325 a de-identification model is applied to each of the images image_1 and image_2, outputting de-identified representations 1 and 2 at steps 1330 and 1335 respectively. These two de-identified representations 1330, 1335 are fed into a same-not-same model 1340. Same-not-same model 1340 estimates whether representations 1330, 1335 are of images of the same person or not, outputting the result at 1345 regarding its decision. At binary classification loss step 1350, the output at step 1345 is compared with the label generated at step 1320 to determine whether there is a match (i.e. if the images are determined to be of the same person in step 1345, are they actually of the same person as noted in step 1320. If there is no same-not-same model that performs better than random chance, then it can be determined that the de-identification is perfect.

Figure 14:
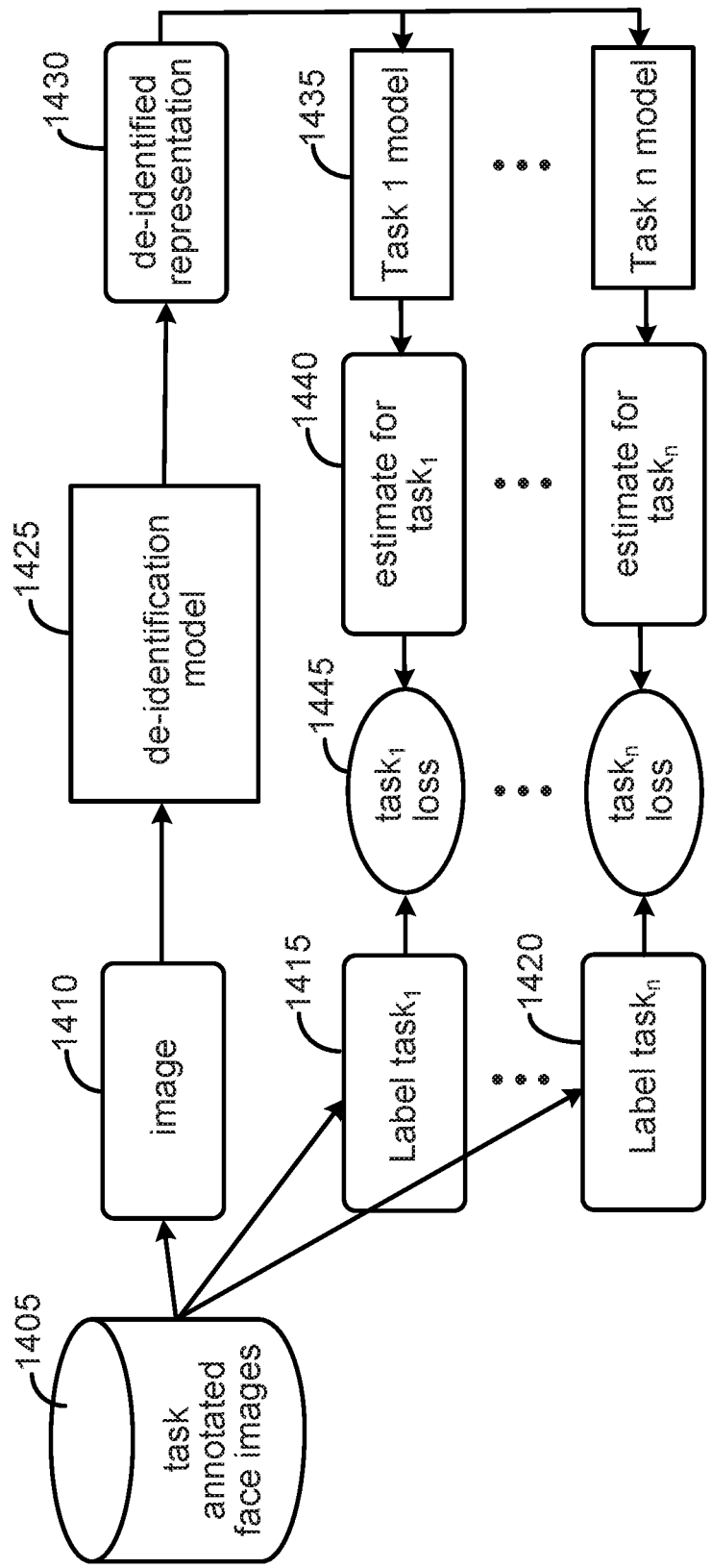
FIG. 14 depicts a possible approximation for joint optimization of the two models (FIGS. 10 and 12), and operates in a block-wise optimization of the parameters in accordance with an exemplary embodiment of the invention.

The same-not-same model and the de-identification model described above "compete" with each other. The de-identification model tries to mask the identity (making it harder to determine what is going on, while the same-not-same model tries to determine what is going on between the images. FIG. 14, depicts a possible approximation for joint optimization of the two models, and operates in a block-wise optimization of the parameters. The system preferably alternates 1) fixing the parameters of the de-identification and training a same-not-same model to distinguish identities in its outputs and then 2) freezing the same-not-same parameters and optimizing the de-identification model to "fool" the fixed same-not-same model. At 1405 a set of task annotated face images are shown. Each image 1410 is extracted and fed through a proposed de-identification model 1425. One or more task labels 1415, 1420 are also determined for each image. A de-identified representation of the image 1430 is extracted from de-identification model 1425, and a particular one or more task models 1435 are performed. A resulting estimate 1440 for each task model is determined, and at step 1445, each result is compared to a corresponding task label 1415, 1420 to determine a minimum number of task losses. Once the task losses have been reduced as much as possible, the system has been properly calibrated.

Thus, models may be trained for known tasks 1435 (task_1 . . . task_n) using supervised data. i.e. data which includes annotation for the tasks of interest. The task models are optimized to minimize losses 1445 (loss_1 . . . loss_n) which are appropriate losses for each one of the tasks of interest. A possible strategy to jointly optimize the task models and the de-identification model is block-wise coordinate optimization. The de-identification model parameters may be fixed, and the task models trained to minimize the sum or weighted sum of the individual task losses. Given fixed task models, the parameters of the de-identification model may be adjusted to improve performance on the task losses.

Therefore, in accordance with various embodiments of the present disclosure system and method are provided in which, among other results, images of faces can be de-identified in a manner that retains relevant information so that a maximum number of future questions can be properly answered.

Use of the system may be employed in a controlled or natural setting, and therefore may improve patient engagement, as the system may be used at any location. Additionally, the user's environment may be measured in, for example, a recovery situation, to determine whether user is in a most desirable environment to aid such recovery.

Therefore, in accordance with various embodiments of the present disclosure system and method are provided in which, among other results, images of faces can be stored in a manner that retains relevant information so that a maximum number of future questions can be properly answered.

This specification uses the term "configured" in connection with apparatuses, processors modules, systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them.

Embodiments of the subject matter described in this specification can be implemented as one or more computer programs, i.e., one or more modules of computer program instructions encoded on a tangible non transitory program carrier for execution by, or to control the operation of, data processing apparatus. Alternatively, or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit). For example, the processes and logic flows can be performed by and apparatus can also be implemented as a graphics processing unit (GPU).

Computers suitable for the execution of a computer program include, by way of example, general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

It should be noted that any of the above-noted techniques and systems may be provided in combination or individually. Furthermore, the system may be employed in mobile devices, computing devices, cloud based storage and processing. Camera images may be acquired by an associated camera, or an independent camera situated at a remote location. Processing may be similarly provided locally on a mobile device, or a remotely at a cloud-based location, or other remote location. Additionally, such processing and storage locations may be situated at a similar location, or at remote locations.

What is claimed:

1. A method for monitoring a state of an individual, the method comprising:
obtaining a video record of the individual performing a physical activity;
de-identifying the video record, wherein de-identifying the video record comprises
identifying a subset of points to be extracted from the video record, the subset of points allowing for future analysis of the physical activity, and
storing the subset of points without storing the video record to inhibit re-identification of the individual in the video record;
measuring the physical activity as recorded by the stored subset of points;
comparing the measured physical activity to an expected physical activity to obtain a comparison result; and
diagnosing one or more aspects of disease based on the comparison result.

2. The method of claim 1, comprising storing non-visual information associated with the video record and selected from one or more sensor outputs.

3. The method of claim 1, comprising:
identifying a subset of sensors of a plurality of sensors applicable to recognize a particular disease;
recording a second physical activity by the subset of sensors; and
analyzing the recorded second physical activity to confirm a presence or absence of the particular disease.

4. The method of claim 1, comprising:
recording a second physical activity by a plurality of sensors; and
analyzing the recorded second physical activity to determine a presence or absence of one or more possible recognized diseases.

5. The method of claim 1, wherein the subset of points comprises facial keypoints.

6. The method of claim 1, wherein the subset of points corresponds to one or more portions of a face of the individual.

7. The method of claim 1, comprising displaying, to a user, an interface by which the user is able to modify a number of points to be included in the subset of points.

8. The method of claim 1, comprising:
blurring a portion of the video record; and
storing the blurred portion in association with the stored subset of points.

9. A system for monitoring a state of an individual, comprising:
a video capture device;
one or more processors; and
a memory storing one or more non-transitory, computer-readable instructions that, when executed by the one or more processors, cause the one or more processors to perform operations comprising:
obtaining, from the video capture device, a video record of the individual performing a physical activity;
de-identifying the video record, wherein de-identifying the video record comprises
identifying a subset of points to be extracted from the video record, the subset of points allowing for future analysis of the physical activity, and
storing the subset of points without storing the video record to inhibit re-identification of the individual in the video record;
measuring the physical activity as recorded by the stored subset of points;
comparing the measured physical activity to an expected physical activity to obtain a comparison result; and
diagnosing one or more aspects of disease based on the comparison result.

10. The system of claim 9, wherein the operations comprise storing non-visual information associated with the video record and selected from one or more sensor outputs.

11. The system of claim 9, comprising a plurality of sensors, wherein the operations comprise:
identifying a subset of sensors of the plurality of sensors applicable to recognize a particular disease;
recording a second physical activity by the subset of sensors; and
analyzing the recorded second physical activity to confirm a presence or absence of the particular disease.

12. The system of claim 9, comprising a plurality of sensor, wherein the operations comprise:

recording a second physical activity by the plurality of sensors; and analyzing the recorded second physical activity to determine a presence or absence of one or more possible recognized diseases.

13. The system of claim 9, wherein the subset of points comprises facial keypoints.

14. The system of claim 9, wherein the subset of points corresponds to one or more portions of a face of the individual.

15. The system of claim 9, comprising a display, wherein the operations comprise displaying, to a user, by the display, an interface by which the user is able to modify a number of points to be included in the subset of points.

16. The system of claim 9, wherein the operations comprise:

blurring a portion of the video record; and storing the blurred portion in association with the stored subset of points.

\* \* \* \* \*